United States Patent

Sugino et al.

[11] Patent Number: 5,593,558
[45] Date of Patent: Jan. 14, 1997

[54] OXYGEN CONCENTRATION DETECTOR

[75] Inventors: Hiroshi Sugino, Chita-gun; Yasumichi Hotta, Mie-gun; Namitsugu Fujii, Yokkaichi; Masahiro Shibata; Hiromi Sano, both of Nagoya, all of Japan

[73] Assignee: Nippondenso Co., Ltd., Kariya, Japan

[21] Appl. No.: 467,144

[22] Filed: Jun. 6, 1995

[30] Foreign Application Priority Data

Jun. 9, 1994 [JP] Japan .................................. 6-127509
Aug. 8, 1994 [JP] Japan .................................. 6-208025

[51] Int. Cl.$^6$ .................................................. G01N 27/26
[52] U.S. Cl. ...................... 204/429; 204/425; 204/419; 427/103; 427/126.3; 427/245; 427/372.2; 427/446; 427/453; 427/454
[58] Field of Search .................................. 204/429, 425, 204/419; 427/126.3, 103, 446, 453, 454, 245, 372.2

[56] References Cited

U.S. PATENT DOCUMENTS

| | | | |
|---|---|---|---|
| 4,066,413 | 1/1978 | Segawa et al. | 23/254 E |
| 4,177,112 | 12/1979 | Suzuki et al. | 204/429 |
| 4,402,820 | 9/1983 | Sano et al. | 204/429 |
| 4,584,086 | 4/1986 | Hayakawa et al. | 204/429 |
| 5,160,598 | 11/1992 | Sawada et al. | 204/429 |
| 5,310,575 | 5/1994 | Friese et al. | 204/429 |

FOREIGN PATENT DOCUMENTS

| | | |
|---|---|---|
| 50-14396 | 2/1975 | Japan . |
| 50-149729 | 12/1975 | Japan . |
| 53-13980 | 2/1978 | Japan . |
| 61-153561 | 7/1986 | Japan . |
| 62-187245 | 8/1987 | Japan . |
| 215017 | 4/1990 | Japan . |
| 576575 | 10/1993 | Japan . |
| 6174683 | 6/1994 | Japan . |

*Primary Examiner*—Bruce F. Bell
*Attorney, Agent, or Firm*—Cushman, Darby & Cushman IP Group of Pillsbury; Madison & Sutro LLP

[57] ABSTRACT

An oxygen concentration detector includes a one-end closed cylindrical oxygen sensing element having an inside electrode, outside electrode provided on the inner side and outer side respectively, an electrode protecting layer made up of ceramics porous member provided further outside the outside electrode, and a trap layer 1 of ceramics porous member having a surface roughness of 20 to 100 μm measured according to a 10 point mean roughness measurement and provided outside the electrode protecting layer is employed. By dipping the to-be-detected gas side surface of an oxygen sensing element into a slurry with coarse heat-resisting metal oxide particles, 2 to 50 μm in average grain size, dispersed, depositing the slurry on the surface of a protective layer of an oxygen sensor element, thereafter drying and baking the deposit, a porous poisonous substance trap layer, 10 to 500 μm thick, is formed. The dipping is performed after a previous degassing and strong stirring of said slurry and the stop of stirring.

23 Claims, 12 Drawing Sheets

OXYGEN CONCENTRATION DETECTOR

CROSS REFERENCE TO RELATED APPLICATIONS

This application is based upon and claims priority from Japanese Patent Application No. 6-127509 filed Jun. 9, 1994 and Japanese Patent Application No. 6-208025 filed Aug. 8, 1994, with the contents of each document being incorporated herein by reference.

BACKGROUND OF THE INVENTION

1. Field of the Invention

The present invention relates to oxygen concentration detectors (oxygen sensor, air-fuel ratio sensor, leak sensor and such like sensors) effective in use for the control of combustion in an internal-combustion engine.

2. Description of the Related Art

As gas detectors for detecting the oxygen concentration in exhaust gas of an automobile internal-combustion engine, a gas detector using a $ZrO_2$ solid electrolyte, say, of oxygen concentration electromotive force type has been known since former days and such has been widely made practicable. As the above electromotive force type of gas detector, there is such an oxygen concentration detector as disclosed in Japanese Examined Patent Publication No. 2-15017.

The relevant oxygen concentration detector has an oxygen sensing element provided on the tip thereof, which sensing element is a bottomed cylinder comprising an inside electrode, solid electrolyte sintered body, outside electrode, and electrode protecting layer formed in sequence, whereas a heater is inserted in the internal cavity of the above oxygen sensing element. The above electrode protecting layer is formed of ceramic coating layer, say $Al_2O_3$ layer provided on a ceramic coating layer. Exhaust gas passes through the above ceramic coating layer or the above $Al_2O_3$ layer and reaches to the above outside electrode to provide a sensor output. Under certain practical conditions, however, the outermost surface of the above oxygen sensing element is coated with a deposit originating from exhaust gas. This deposit comprises fine particles or glassy films composed of oil components of P, Ca, Zn, Si or the like, and gasoline mixture components of K, Na, Pb or the like, while the surface of the above electrode protecting layer is coated with the above deposit, thereby preventing exhaust gas from scattering to the above outside electrode. This causes a deterioration of quality, such as a decrease in output or a decrease in response. Accordingly, there is a problem in that sticking of such a deposit causes said gas detector to fail in stable sensor characteristic for a long time.

Thus, to solve the problems mentioned above, improving proposition, for example, of having a poisonous substance trap layer comprising a relatively porous flame fusion film or $Al_2O_3$ particles of several μm grain size provided on the above electrode protecting layer, thereby eliminating the clogging.

First, an oxygen sensing element has been proposed in which the surface exposed to exhaust gas is coated with an insulating coat comprising a metal oxide, heat-resisting, porous, and permeable for the gas to be detected, said insulating film made to bear a catalyst (Japanese Patent Application Laid-Open No. 52-73089). As the above insulating film, $\gamma$-$Al_2O_3$, $ZrO_2$, MgO or the like is employed, whereas Pt, Pd, Rh or the like is employed as the above catalyst. The above insulating coat prevents a poisonous component from sticking directly to the above oxygen sensing element and therefore the gas detector itself improves in durability.

Secondly, an oxygen sensor has been proposed in which on the surface of the electrode for the gas to be detected in an oxygen sensing element is provided a protective layer mixed with $\gamma$-alumina particles for covering the catalyst layer (Japanese Patent Application Laid-Open No. 61-153561). According to this constitution, the Pb component contained in exhaust air is absorbed to a highly absorptive $\gamma$-$Al_2O_3$ particles if permeating the protective layer, so that the poisoning by Pb on the catalyst layer can be prevented.

Thirdly has been proposed a method for forming a relatively porous trap layer for poisoned materials on the surface of an oxygen sensing element by flame fusion coating process (Japanese Patent Application Laid-Open No. 53-13980); fourthly, a method for forming a trap layer containing $\gamma$-$Al_2O_3$ several μm in grain size for poisons on the surface of an oxygen sensing element (Japanese Patent Application Laid-Open No. 621-153561); fifthly, a method for forming a trap layer comprising a Pt-bearing catalytic layer for poisoned materials on the surface of an oxygen sensing element (Japanese Examined Patent Publication No. 5-76575); and sixthly, a method for forming a Pb-made trap layer having a fixed pore volume and thickness for poisons on the surface of an oxygen sensing element (Japanese Patent Application Laid-Open No. 62-187245).

These gas detectors of the above propositions as described above are effective especially for the detection of exhaust gas in an internal-combustion engine, that is, has a great effect on the capture of poisonous components, such as Pb P S Si and Zn Also, they are effective in preventing the poisonous deterioration of interior catalysts and in greatly promoting the durability.

In recent years, however, further improvement in fuel cost and performance for internal-combustion engines has been forwarded corresponding to the global environment policy and so the using surroundings of a gas detector become severer. The using temperature of gas detectors becomes higher and the amount of poisonous components increases. Consequently, under high temperatures, the trapped poisonous components react with each other, or fuse and form an intrinsically air-tight glassy deposition coat on the surface of oxygen sensing elements on following cooling, causing a clogging.

Based upon a intensive study for coping with these circumstances, it is one object of the present invention to provide an oxygen concentration detector free from clogging and excellent in durability, that is, capable of maintaining a stable sensor output for a long period, by preventing the formation of a dense air-tight glassy deposit coating on the surface of oxygen sensing elements.

SUMMARY OF THE INVENTION

To solve the problems, the present invention provides an oxygen concentration detector includes: an oxygen sensing element having an inside and outside electrodes provided on the inner side and outer side respectively and having an electrode protecting layer made out of ceramics porous member provided further outside the outside electrode; output pickup means electrically connected to said inside electrode on the inner side of said oxygen sensing element; at least one housing for accommodating said oxygen sensing element; and a trap layer of ceramics porous member having a surface roughness of 20 to 100 μm measured according to a 10 point average roughness technique and provided outside the electrode protecting layer.

By employing an oxygen concentration detector fabrication method comprising the steps of: depositing a slurry, in which heat-resisting particles comprising one or more of globular, block, fiber, foam, pillar, or needle $\alpha$-$Al_2O_3$, $\gamma$-$Al_2O_3$, murite, $MgO.Al_2O_3$ spinel, an inorganic binder, and a dispersion medium are dispersed in water, onto an electrode protecting layer of a cylindrical oxygen sensing element, closed at one end, comprising inside and outside electrodes on the inner and outer faces, respectively, and an electrode protecting layer made of ceramics porous member further outside the outside electrode by dipping or spraying; and baking it at 500° to 900° C. for forming a trap layer as set forth in Claim 6; an oxygen concentration detector according to the present invention can be provided.

Further, according to the inventors research, it is considered that formation of a continuous coat is prevented even if a glassy deposition sticks to a trap layer, thereby securing intercommunicating pores, by selecting a poisonous substance trap layer of porous material, larger in surface roughness and by increasing the thickness thereof. When providing the poisonous substance trap layer with such a large thickness in said oxygen sensing element, the oxygen sensing element may be dipped into the slurry where particles are dispersed.

However, rough particles must be used to make a trap layer porous. Such particles are apt to sediment in the slurry and therefore it is difficult to apply a poisonous substance trap layer in a uniform and homogeneous way.

In other words, a slurry containing rough particles can be dispersed to some extent by adding a binder and dispersant or by adjusting the pH (potential of hydrogen), but the sedimentation of particles cannot completely be prevented. Accordingly, stirring is required for uniformly dispersing the particles in a slurry. However, on dipping an oxygen sensing element while stirring, particles are unlikely to stick to the surface against which the flow strikes in the oxygen sensing element dipped under influence of the stirring flow velocity, thereby decreasing the thickness of a poisonous substance trap layer. As a result, a variance appears in the thickness of the poisonous substance trap layer.

On the contrary, on allowing the slurry to stand at rest without stirring, the sedimentation of particles occurs and particles fail to stick. Or, a continuous dipping causes a disadvantage in that the weight of deposit formed decrease and the trap layer becomes thinner with the elapse of time.

Increase in the thickness of a poisonous substance trap layer causes another difficult problem in that air bubbles are apt to be generated and a large bubble happens to be formed in the trap layer on baking, thus making the part thereof useless.

Such a disadvantage results into a decrease in the poisoned-material trapping effect and the function of a film. Furthermore, the initial characteristic of an oxygen sensor element becomes unstable and the sensor characteristic varies.

Thus, the present invention further presents a method for producing an oxygen sensor element, capable of forming a poisonous substance trap layer, homogeneous in film thickness and scarce in air bubbles, superior in the poisonous substance trapping effect, and stable in sensor characteristic.

An oxygen sensor element fabrication method according to the present invention includes the steps of: making an oxygen sensing element by forming a pair of electrodes on the respective surfaces of a solid electrolyte and coating the surface on the side of detecting a gas in said solid electrode with a porous protective layer; depositing a slurry in which heat-resisting metal oxide particles, 2 to 50 μm in average grain size, are dispersed onto the surface of said protective layer by dipping; and forming a porous poisonous substance trapping layer, 10 to 500 μm thick, by drying and baking said heat-resisting metal oxide particles wherein said dipping is performed after the degassing and previous strong stirring of said slurry, and the completion of stirring.

The remarkable point in the present invention is to degass a slurry containing heat-resisting metal oxide particles, to then uniformly disperse heat-resisting metal oxide particles by stirring and to dip an oxygen sensing element in the slurry after the completion of stirring in forming a poisonous substance trapping layer on the protective layer of an oxygen sensing element.

By making the surface of the above trap layer uneven to an overall extent, a deposit is interrupted at the boundary between a concave portion and convex portion, thereby eliminating the overall coverage over the whole surface of the trap layer, even when said glassy deposits on the surface of the trap layer under a stringent using environment, so that the opening of opened pores near the surface is secured for certain and no clogging occurs.

That is, even though a deposit originating from poisonous substances sticks to the surface of the above trap layer and a dense glassy layer is formed, numerous openings are always maintained and the gas to be detected is not prevented from reaching to the electrodes.

Also, the above deposit can be prevented from reaching an electrode protecting layer formed inside the trap layer. In this way, the gas to be detected can easily reach from the measuring atmosphere through the above trap layer and the above electrode protecting layer to the electrodes, enabling long-term maintenance of stabilized sensor output.

Furthermore, in an oxygen sensor element fabrication method a slurry is degassed in advance before the dipping. On degassing, the air bubbles in the slurry disappear.

After the above degassing, the slurry is strongly stirred. In this way, the coarse heat-resisting metal oxide particles contained in the slurry disperse at a uniform concentration into the slurry.

After the stop of the above stirring, the surface of the protective layer of the oxygen sensing element is dipped in the above slurry. This slurry has heat-resisting metal oxide particles dispersed uniformly in it and is at rest. Thus, no sedimentation of heat-resisting metal oxide particles is found.

Consequently, a slurry of nearly uniform thickness can be deposited on the surface of the protective layer and therefore a poisonous substance trap layer of nearly uniform thickness can be formed by baking this deposit.

According to the present invention, a poisonous substance trap layer, uniform in film thickness and scarce in air bubbles can be formed and a method for fabricating an oxygen sensor excellent in trapping a poisonous substance and stable in sensor characteristic can be provided.

BRIEF DESCRIPTION OF THE PREFERRED EMBODIMENTS

Figure 1:
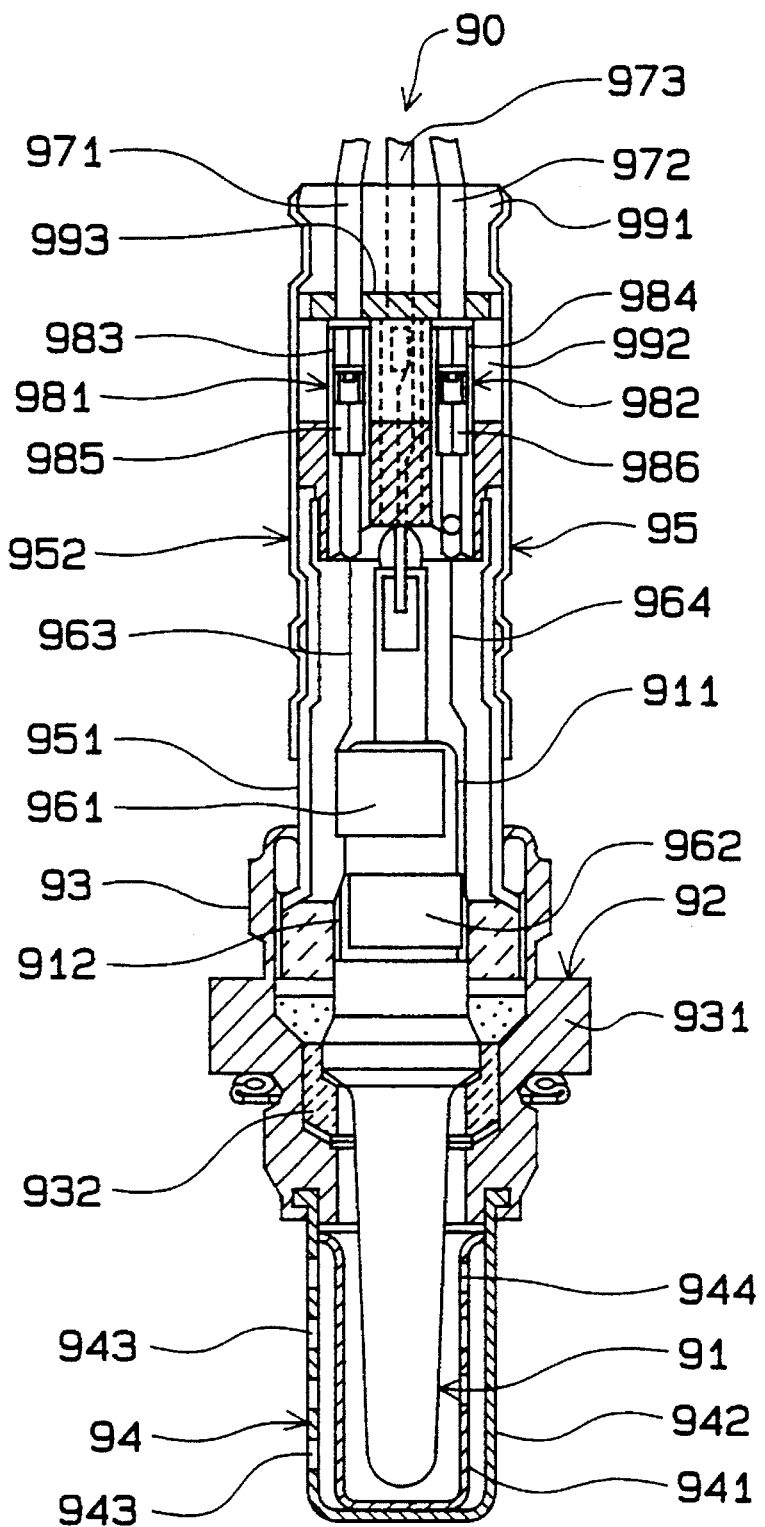
FIG. 1 is a sectional view of an oxygen concentration detector according to the present invention.

FIG. 1 is to illustrate the constitution of an oxygen concentration detector 90 according to the present invention. In FIG. 1, the oxygen concentration detector 90 comprises an oxygen sensor element 91 forming an electrochemical cell and a housing 92 for accommodating the oxygen sensor element 91. The housing 92 comprises a body 93 provided with flange 931 about at the center, an exhaust cover 94 to be inserted into an exhaust passage under the body 93, and an atmospheric cover 95 in contact with the atmosphere over the body 93. The exhaust cover 94 comprises an inner stainless steel cover 941 and outer cover 942, where an exhaust ports 943, 944 are provided on the inner cover 941 and the other covers 942.

On the other hand, the atmospheric cover 95 comprises a main cover 951 attached to the body 93 and a subcover 952 for covering the rear end of the main cover 951, where an atmosphere intake ports not shown are provided on the main cover 951 and the subcover 952. And, the oxygen concentration detector 90 is supported inside the body 93 through insulating member 932. To the inside electrode 911 and the outside electrode 912 (incidentally, the inner electrode 911 and the outer electrode 912 are represented as an inner electrode 32 and outer electrode 31 in the following embodiments 1 to 4), metal plate terminals 961, 962 for supporting them as enclosed are connected, while the plate terminals 961, 962 are connected to outlet lead wires 971, 972. That is, on the plate terminals 961, 962, strip terminal members 963, 964 are provided in such a manner as to protrude toward the plate terminals 961 and 962. The terminals 963, 964 are connected to one end 985, 986 of connectors 981, 982 with the other end 983, 984 connected to the lead wires 971, 972, respectively. The plate terminals 961, 962, made by cylindrically deforming T-shaped metal plate, hold the inner electrode 911 or the outer electrode 912 therebetween. By a spring elastic force of the metal plates, an appropriate contact pressure is given between the plate terminals 961, 962, the inner electrode 11 and the outside 912. On the other hand, since a stretching force in an axial direction of the oxygen sensor acts on the lead wires 971, 972, the plate terminals 961, 962 are pulled via the connectors 981, 982 and so may happen to slide in an axial direction. To prevent this, a stopper 993 sandwiched between the rubber bushings 991, 992 is provided at the end of the oxygen sensor 90. The stopper 993 serves to prevent the shift of the connectors 981, 982 and are formed of a resin material for maintaining the insulation between the lead wires 971 and 972. Incidentally, numeral 973 denotes a heater wire for heating the oxygen sensor element 91. The oxygen sensor 90 has the exhaust cover 94 inserted in the exhaust passage and is fixed to the exhaust passage with the flange 931. The oxygen sensor 90 of the constitution described above is a sensor in which an electrochemical cell is made up by installing electrodes on both surfaces of a solid electrolyte comprising oxygen ion conductor, the exhaust gas is introduced in one electrode, the atmosphere is introduced in the other electrode, and the air-fuel ratio is sensed from the potential difference between the electrodes, originating in the oxygen concentration difference between the exhaust gas and atmosphere.

Hereinafter, the principal portion of the present invention will be described.

[Embodiment 1]

The embodiment 1 has revealed that, when a glassy deposition sticks to a convex portion and concave potion, the deposition is interrupted by intentionally making the surface of a poisonous substance trap layer (hereinafter, referred to as trap layer) uneven to eliminate the possibly of the whole surface layer to be covered with deposits and consequently a ventilating route for the exhaust gas is secured.

Figure 2:
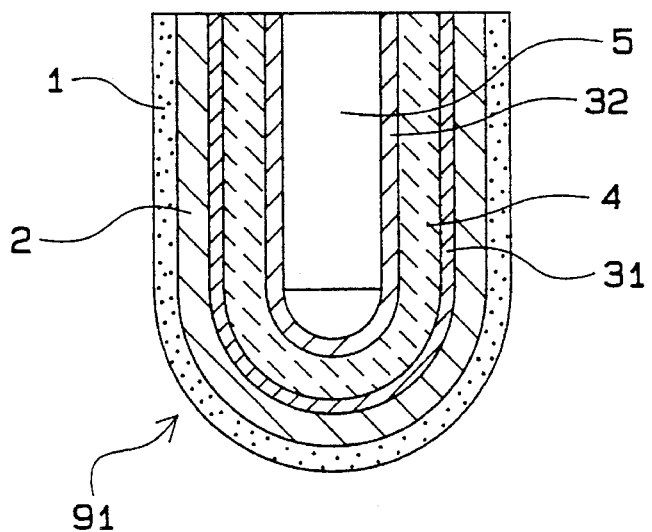
FIG. 2 is a sectional view of an oxygen sensing element, part of an oxygen concentration detector according to the embodiment 1 of the present invention.
Figure 3:
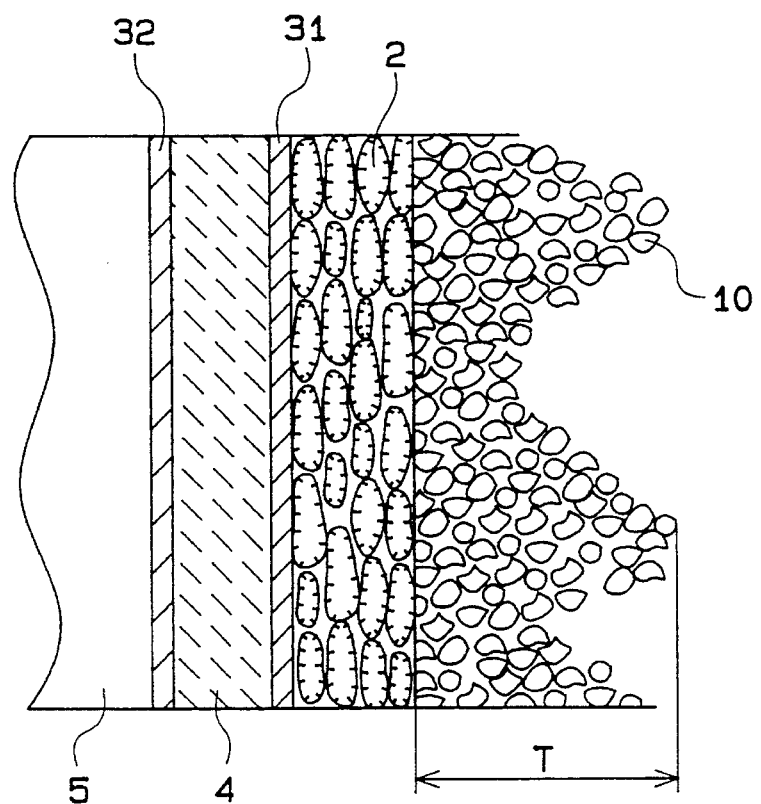
FIG. 3 is an enlarged sectional view of an oxygen sensing element, part of an oxygen concentration detector according to the embodiment 1 of the present invention.

As shown in FIG. 2, the oxygen concentration detector 90 is a sensor of oxygen concentration electromotive force system. The oxygen sensor element 91 comprises a pair of outside electrode 31 and inside electrode 32, a porous electrode-protecting layer 2 for protecting the outside electrode 31 and controlling the diffusion of gas, and a trap layer 1 covering the electrode protecting layer 2, where the trap layer 1 consists of a porous member for trapping poisoned components. The electrode protecting layer 2 is a porous protective layer formed by flame fusion coating of MgO.Al$_2$O$_3$ spinel or the like. The trap layer 1 is a porous member formed of numerous particles as shown in FIG. 3. These particles are thermally stable and continuously combined into the trap layer 1.

Figure 4:
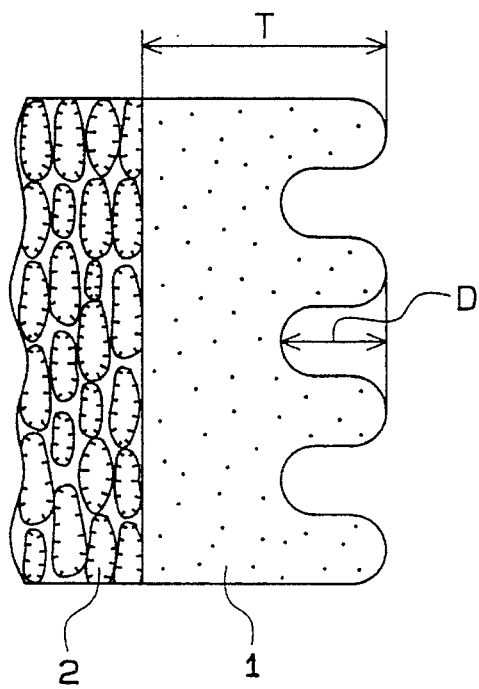
FIG. 4 is a schematic drawing illustrating the concept of an uneven surface by using an enlarged section of a trap layer of an oxygen sensing element, part of an oxygen concentration detector according to the embodiment 1 of the present invention.

FIG. 4 is a partially enlarged cross-sectional view showing the electrode protective layer 2 of the outer electrode 31 formed on the surface of the solid electrolyte 4 comprising the oxygen sensor element 91 of the oxygen concentration detector 90 and the trap layer 1 formed on the protective layer 2.

Figure 5:
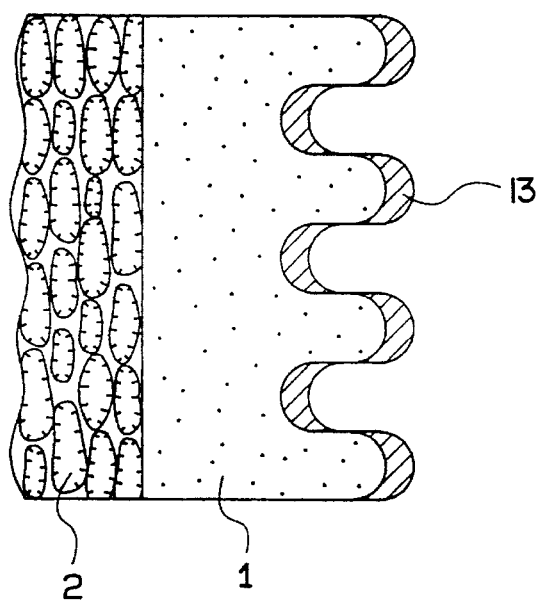
FIG. 5 is a schematic drawing illustrating the sticking aspect of a deposit on the surface of a trap layer of an oxygen sensing element, part of an oxygen concentration detector according to the embodiment 1 of the present invention.

As shown in a schematic diagram of FIG. 4, the surface of the trap layer 1 forms a rugged structure. By making the surface of the trap layer 1 uneven, a glassy deposit 13, even if sticking to the surface of the trap layer 1 (FIG. 5), is interrupted at the boundary between a concave and convex portion, eliminating the possibility of the whole surface layer to be covered with deposits, and consequently the ventilating route of exhaust gas is secured. Using a 10 point mean roughness measurement as defined in Japan Industrial Standard (JIS) B 0601-1982: R$_z$, incorporated herein by reference, the depth of such a recess must be greater than 20 μm measured according to the 10 point mean roughness measurement to obtain a satisfactory effectiveness. "Roughness" as used herein is defined as mean surface roughness measured according to the above-mentioned JIS0601-1982:R$_z$. In case that a depth of less than 20 μm in 10 point mean roughness (R$_z$), if the using time is short, the amount of deposits is small and the opening of opened pores near the surface of the trap layer 1 is maintained, whereas the amount of deposits increases with prolonging using time and thus it is feared a deposit on a convex portion and another deposits on a concave portion come to connect, thereby leading to the occurrence of clogging.

Figure 19:
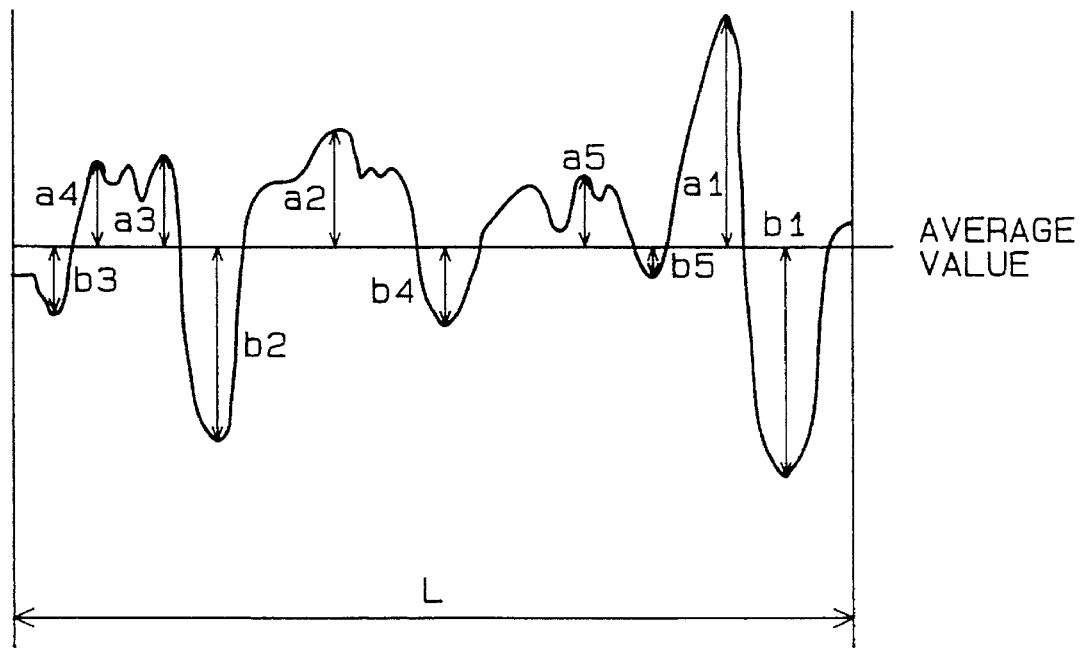
FIG. 19 is an explanatory view of a 10 point mean roughness technique regulated by JIS (Japan Industrial Standard) B0601-1982: $R_z$.
Figure 20:
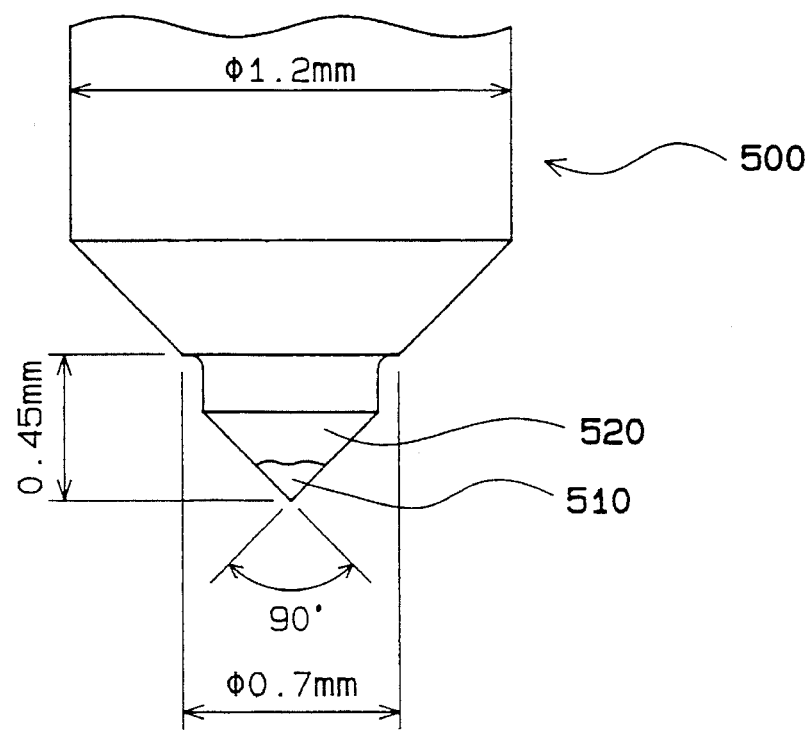
FIG. 20 is an explanatory view of a stylus utilized for the 10 point mean roughness technique.

The 10 point mean roughness (R$_z$) measurement is explained by using FIGS. 19 and 20. A stylus 500 is utilized as shown in FIG. 20. The stylus has a contact head 510 made of diamond at the tip thereof and a base 520 supporting the contact head 510. The tip of the contact head 510 has a sheroidal shape of which carvature is 5 μm in radius. The contact head 510 and the base 520 is unifyed and have a conical shape of which tapered angle is a 90-degree, a diameter of about 0.7 mm and longitudinal length of about 0.45 mm. The stylus is placed at an optional point on the trap layer and measures the surface roughness for a straight length L of 8 mm. Respective length from tops of concave and covex portions to a mean thickness is measured. In particularly, the convex portions larger than the mean thickness are measured from maximum value to fifth largest value (in FIG. 19, a1–a5), and the concave portions smaller than the mean thickness are measured from minimum value to fifth smallest value (in FIG. 19, b1–b5) are measured. And then, the mean value is calculated as follows:

$$\text{mean value} = \frac{(a1 + a2 + a3 + a4 + a5) - (b1 + b2 + b3 + b4 + b5)}{10}$$

The mean value is defined as the 10 point mean surface roughness in the present invention.

The trap layer 1 is formed by adding water and 3 to 20 wt % of inorganic binder and dispersant to 100 wt % of constituent particles to prepare a slurry, depositing this slurry onto the surface of an oxygen sensor element by dipping or spraying, and baking the deposit at 500° to 900° C. Using those particles for preparing the slurry which are 20 μm or more in average grain size and contains not greater than 10 wt % of particles, not greater than 10 μm in grain size, the 10 point mean roughness (R$_z$) for the surface of the trap layer 1 can preferably be obtained at 20 μm or more.

Incidentally, even when the particles not greater than 10 μm in grain size are contained 10% or more, the 10 point mean roughness (R$_z$) can be obtained at 20 μm or more by mixing coarse particles, say, 50 μm or greater in grain size. Controlling the grain size distribution of particles forming the trap layer 1 enables the 10 point mean roughness (R$_z$) to be adjusted. By selecting the content of particles, not greater than 10 μm in grain size, at 10 wt %, however, the 10 point mean roughness can easily be elevated up to 20 mμ or higher. Or, by mixing organic materials, such as resin material, to be scattered on combustion or the like into the slurry at 500° to 900° C. depositing the mixture onto the surface of the oxygen sensor element 91 by dipping and the like, thereafter baking, the 10 point mean roughness (R$_z$) can be adjusted.

The trap layer 1 comprises heat-resisting particles preferably of one or more of α-Al$_2$O$_3$, γ-Al$_2$O$_3$, murite, MgO.Al$_2$O$_3$ spinel. The shape of particles may be selected out of globular, lump, plate, fiber, foam, pillar, needle and the like shapes.

Also, the trap layer 1 can be made up by using secondary particles formed from clusters of primary dense particles, 1 μm or smaller in grain size. The average pore diameter d of the trap layer 1 is larger than that of a porous electrode-protecting layer. Otherwise, it is feared deposits comprising poisoned components clog in the trap layer and cover the surface, thereby making the exhaust gas unable to pass through the trap layer.

The average pore diameter d of the above trap layer 1 is preferably 0.5 μm or greater. Otherwise, the amount of deposits is small and the opening of opened pores near the surface of the above trap layer 1 is maintained while the using time is short, whereas the amount of deposits increases with prolonging using time, so that a continuous deposit layer is formed near the surface of the trap layer, thereby leading to a fear of clogging to occur. In addition, for too large a average pore diameter, it is feared the fine-grained deposits accumulated since formerly pass through a pore to reach the electrode protecting layer, thereby leading to the occurrence of clogging in the electrode protecting layer. Thus, the average pore diameter d ranges preferably from 0.5 to 50 μm.

The thickness T of the above trap layer 1, evidently greater than the surface roughness R$_z$ needed for breaking the continuation of deposits, ranges preferably from 30 to 500 μm. For a thickness smaller than 30 μm, it is feared the above trap layer 1 becomes less than 10 μm thick at the thinnest portion and is too thin to achieve a trapping effect as itself. On the contrary, for a thickness greater than 500 μm, it is feared the above trap layer 1 is so thick that the mutual adherence between the electrode protecting layer and the above layer 1 lowers. In addition, it is also feared the diffusion of exhaust gas in the trap layer itself is prevented, thereby adversely affecting the initial characteristic of a sensor. More preferably, the thickness is 50 to 300 m.

The porosity of the above trap layer 1 is preferably 40 to 80%. For a porosity below 40%, since it is feared the above trap layer 1 is so dense as to cause a clogging, to secure the ventilating route, the surface roughness is made not smaller than, say, 50 μm. For a porosity above 80%, it is feared the strength of the trap layer 1 lowers.

As described in the present embodiment, by making the surface of the above tap layer 1 uneven, a deposit is interrupted at the boundary between a concave portion and convex portion, thereby eliminating the possibility of the whole surface of the trap layer 1 to be covered with the deposit, even when the glassy deposit is generated on the surface of the trap layer 1 under a stringent using environment, so that the opening of opened pores near the surface is certainly secured and no clogging occurs.

That is, even though a deposit originating from poisonous substances stick to the surface of the above trap layer 1 and a dense glassy layer is formed, numerous openings are always maintained and no gas to be detected is prevented from reaching the electrode. In addition, the above deposits have no possibility of reaching the electrode protecting layer formed in the above trap layer 1. Thus, the gas to be detected can pass from the measuring atmosphere through the above trap layer 1 and the electrode protecting layer and so can easily reach the electrode, thereby enabling a stable sensor output to be maintained for a long period.

In accordance with the fabrication method shown above, sensors were fabricated while varying the surface roughness $R_z$ (μm), thickness T (μm), average pore diameter d (μm), and porosity (μm) of the above trap layer 1 to measure the poisonous durability and initial response.

The range of variation was from 5 to 100 μm for surface roughness $R_z$, from 20 to 300 μm for thickness T, from 2 to 50 μm for average pore diameter d, and from 20 to 80% for porosity of the above trap layer 1. The poisonous durability was judged from a changing ratio of sensor response before and after an accelerated poisonous durability test. The changing ratio is decided as ⊙ if below 5%, o if from 5% to 10% (exclusive), Δ if from 10% to 20% (exclusive), x if 20% or greater. The initial response is decided as ⊙ if below 100 ms, o if from 100 ms to 150 ms (exclusive), A if from 150 ms to 200 ms (exclusive), x if 200 ms or greater.

The test conditions for the endurance tests was the continuous repetition of a test condition in which a in-line engine of four 2000 cc cylinders is rotated at 4000 rpm for 30 min after 30 min idling. The durable temperature is 500° to 700° C. Gasoline to be used was a unleaded gasoline to which 5 wt % of engine oil and cleaner is added, while the durable time is 100 hr.

The above response was determined by measuring the gas response time, that is the time taken for a change in output from 0.6 V to 0.3 V at the time of switching over from λ=0.9 to λ=1.0. Measurements were carried out while running an in-line engine of six 2000 cc cylinders assembled with fuel injection devices at 1100 rpm by use of unleaded gasoline. The above measurements shall be performed before and after the endurance test.

This experimental result reveals that the initial response does not deteriorate and a good poisonous durability is obtained when the range of variation is from 20 to 100 μm for surface roughness $R_z$, from 50 to 300 μm for thickness T, from 0.5 to 50 μm for average pore diameter d, and from 40 to 80% for porosity of the above trap layer 1. The results are shown in Table 1.

TABLE 1

| No. | Surface roughness Rz (μm) | Average pore diameter d (μm) | Porosity (%) | Thickness of the trap layer T (μm) | Poisonous durability | Initial response |
|---|---|---|---|---|---|---|
| 1 | 5 | 2 | 20 | 20 | x | o |
| 2 | 10 | 3 | 30 | 30 | x | ⊙ |
| 3 | 15 | 5 | 40 | 50 | Δ | o |
| 4 | 20 | 5 | 50 | 30 | Δ | ⊙ |
| 5 | 20 | 5 | 50 | 50 | o | ⊙ |
| 6 | 20 | 5 | 50 | 100 | ⊙ | ⊙ |
| 7 | 30 | 10 | 50 | 100 | ⊙ | ⊙ |
| 8 | 50 | 10 | 50 | 70 | o | ⊙ |
| 9 | 50 | 10 | 50 | 100 | ⊙ | o |
| 10 | 50 | 10 | 50 | 200 | ⊙ | o |
| 11 | 50 | 15 | 55 | 100 | ⊙ | ⊙ |
| 12 | 50 | 15 | 55 | 200 | ⊙ | o |
| 13 | 50 | 15 | 55 | 300 | ⊙ | Δ |
| 14 | 70 | 25 | 60 | 100 | o | ⊙ |
| 15 | 70 | 30 | 65 | 150 | ⊙ | ⊙ |
| 16 | 80 | 40 | 70 | 200 | ⊙ | o |
| 17 | 100 | 50 | 80 | 300 | ⊙ | o |

[Embodiment 2]

The present embodiment is a modification of the oxygen concentration detector 90 shown in FIG. 4 in which the poisonous durability is improved by forming a two-layer structure comprising a second trap layer 12 made by modifying the trap layer 1 to rugged-surface structure and a first trap layer 11 denser than the trap layer 12, and the content thereof will be hereinafter described in full detail.

Figure 6:
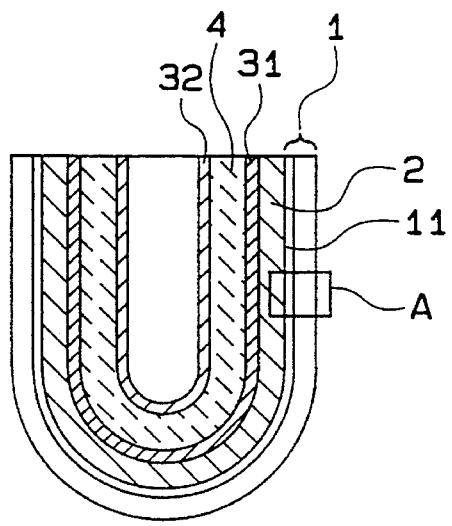
FIG. 6 is a sectional view of an oxygen sensing element, part of an oxygen concentration detector according to the embodiment 2 of the present invention.
Figure 7:
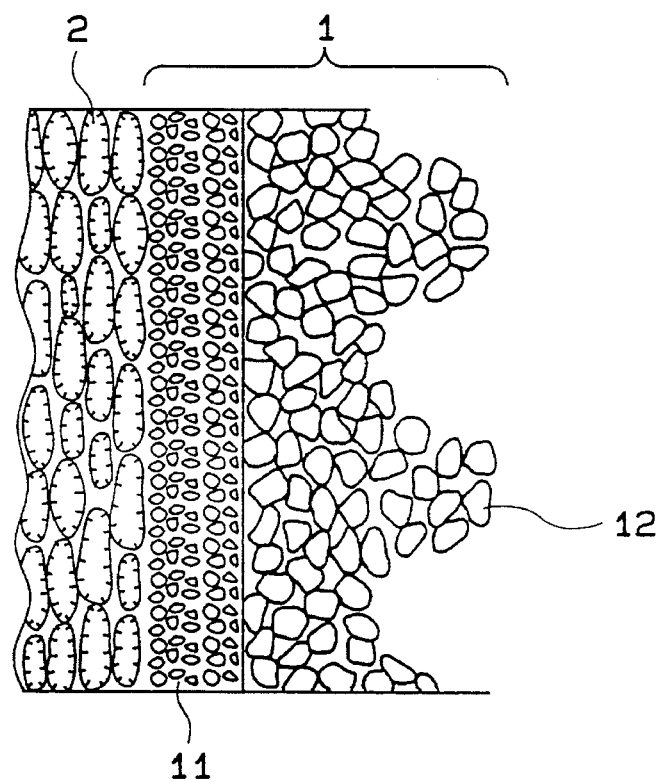
FIG. 7 is an enlarged sectional view of an oxygen sensing element, part A of an oxygen concentration detector according to the embodiment 2 of the present invention.

As shown in FIG. 6, the oxygen sensing element 91 comprises a pair of outside electrode 31 and inside electrode 32, a porous electrode-protecting layer 2 for protecting the outside electrode 31 and controlling the diffusion of gas, and the first trap layer 11 covering the electrode protecting layer 2 and more porous than the electrode protecting layer 2, and the second trap layer 12 covering the first trap layer 11, more porous than the fist trap layer 11 and having rough pores. The first trap layer 11, and the second trap layer 12 comprise porous members for trapping a poisonous component. The electrode protecting layer 2 is a porous protective layer formed by flame fusion coating of MgO.Al$_2$O$_3$ spinel or the like. As shown in FIG. 7, the first trap layer 11 and the second trap layer 12 are porous members formed of numerous particles. FIG. 4 is a partially enlarged cross-sectional view showing the electrode protective layer 2 of the outer electrode 31 formed on the surface of the solid electrolyte 4 comprising the oxygen sensor element 91 of the oxygen concentration detector 90 and the trap layer 1 formed on the protective layer 2. These particles are thermally stable and continuously combined to form the first trap layer 11 and the second trap layer 12. The trap layer 1 comprising such two layers is formed as follows: First, add 3 to 20 wt % of alumina sol as inorganic binder as well as dispersant and water to 100 wt % of γ-$Al_2O_3$ particles, 4 μm in average grain size, to form a slurry, deposit the slurry on the surface of the oxygen sensing element by dipping or spraying, further bake the deposit at 500° to 900° C. to form the first trap layer 11. Next, similarly add 3 to 20 wt % of alumina sol as inorganic binder as well as dispersant and water to 100 wt % of γ-$Al_2O_3$ particles, 20 μm in average grain size, to form a slurry, deposit the slurry on the surface of the oxygen sensing element by dipping or spraying, further bake the deposit at 500° to 900° C. to form the second trap layer 12.

As with the embodiment 1, the surface of the trap layer 12 is of rugged structure. The depth of such a recess is above 20 μm or deeper in the representation of 10 point average roughness ($R_z$). The average pore diameter d of the second trap layer 12 is 0.5 to 50 μm.

The thickness T of the second trap layer 12 is 30 to 300 μm. The porosity of the second trap layer 12 is 40 to 80%.

The trap layer 11 is mainly for the purpose of trapping the fine deposits accumulated since formerly and the average pore diameter d is desired to be larger than that of the electrode protecting layer comprising a porous member, and preferably 0.1 to 0.5 μm. For average pore diameter below 0.1 μm, it is feared a deposit composed of poisonous component causes a clogging in the trap layer 11, thereby making the exhaust gas unable to pass. From a standpoint of trapping a fine poisonous substance, the average pore diameter is preferably smaller than 0.5 μm. The porosity of the first trap layer 11 is preferably 15 to 50%. For a porosity below 15%, it is feared the first trap layer 11 is so dense as to be clogged with poisonous components. To surely trap a fine poisonous substance, the porosity is preferably below 50%. The thickness T of the first trap layer 11 is preferably 5 to 100 μm. For a thickness below 5 μm, it is feared the first trap layer is so thin as to lose a trapping effect. For a thickness above 100 μm, it is feared a harmful influence is exerted on the initial sensor characteristics. The first trap layer 11 and the second trap layer 12 each preferably comprises heat-resisting particles of one or more of α-$Al_2O_3$, γ-$Al_2O_3$, murite, $MgO.Al_2O_3$ spinel, and $TiO_2$. The shape of particles may be selected out of globular, lump, plate, fiber, foam, pillar, needle and the like shapes.

Figure 8:
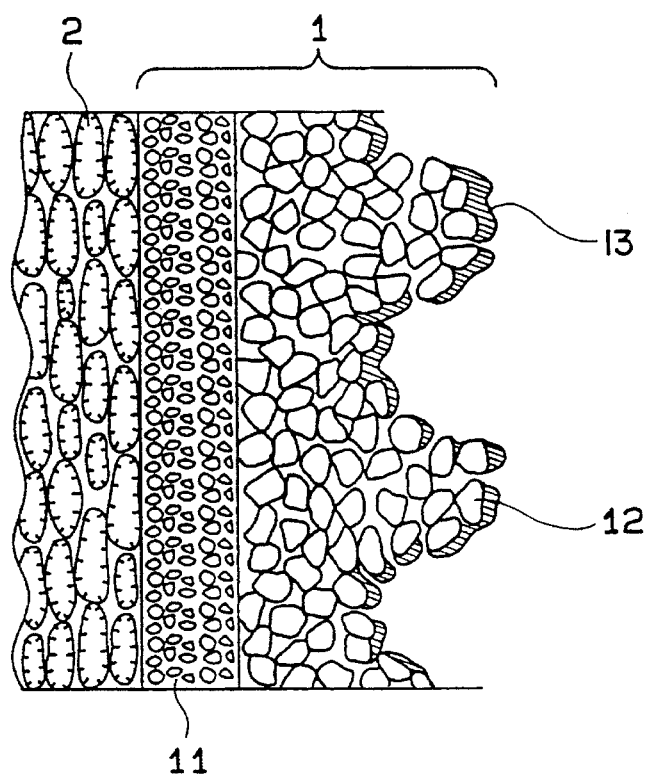
FIG. 8 is a schematic drawing illustrating the sticking aspect of a deposit on the surface of a trap layer of an oxygen sensing element, part of an oxygen concentration detector according to the embodiment 2 of the present invention.

As described above, on installing the trap layer 1 of two-layer structure, even if a glassy poisonous substance 13 is deposited (FIG. 8), the deposit is interrupted at the boundary between a concave portion and convex portion by making the surface of the second trap layer 12 uneven, thereby eliminating the possibility of the whole surface to be covered with the deposit in the trap layer 1, and consequently the ventilating route of exhaust gas is secured. Furthermore, it is feared that fine deposits pass through the second trap layer 12, leading to clogging of the relatively dense electrode protecting layer because the second layer is very porous, but these fine deposits are trapped in the first trap layer 11 and so this fear produces no problem.

Because of having a denser structure than that of the first trap layer 12, the second trap layer can effectively trap fine poisonous substances accumulated since formerly and the total thickness of the trap layer 1 can be made small. That is, modifying the trap layer 1 to a double layer structure makes the strongest effect of trapping a poisonous substance expectable and enables a stable sensor characteristic to be maintained for a long period.

In accordance with the fabrication method shown above, oxygen concentration detectors were fabricated while varying the average pore diameter d (μm), porosity (%), and thickness (T) of the first trap layer and the average pore diameter d (μm), porosity (%), and thickness (T) of the second trap layer as shown in Table 2, and the poisonous durability and initial response was measured. As a result, good results were obtained in the range of 0.1 to 0.5 μm for average pore diameter, 15 to 50% for porosity, and 10 to 50 μm for thickness (T) of the first trap layer 11, and 20 to 100 μm for surface roughness $R_z$, 3 to 50 μm for average pore diameter, 50 to 80% for porosity, and 50 to 300 μm for thickness (T) of the second trap layer 12. Table 2 shows the obtained results. The poisonous durability was judged from a varying rate of sensor response before and after an accelerated poisonous durability test. The varying ratio is decided as ◎ if below 5%, o if from 5% to 10% (exclusive), Δ if from 10% to 20% (exclusive), x if 20% or greater. The initial response is decided as ◎ if below 100 ms, o if from 100 ms to 150 ms (exclusive), Δ if from 150 ms to 200 ms (exclusive), x if 200 ms or greater. Measurements on endurance test conditions and response were carried out using a similar method to that of the embodiment 1.

TABLE 2

| | 2nd trap layer | | | | 1st trap layer | | | | |
| --- | --- | --- | --- | --- | --- | --- | --- | --- | --- |
| No. | Surface roughness Rz (μm) | Average pore diameter d (μm) | Porosity (%) | Thickness of the trap layer T (μm) | Average pore diameter d (μm) | Porosity (%) | Thickness of the trap layer T (μm) | Poisonous durability | Initial response |
| 18 | 20 | 5 | 50 | 30 | 0.2 | 20 | 10 | o | ◎ |
| 19 | 20 | 5 | 50 | 30 | 0.5 | 40 | 20 | ◎ | ◎ |
| 20 | 50 | 10 | 50 | 70 | 0.1 | 15 | 10 | o | ◎ |
| 21 | 50 | 10 | 50 | 70 | 0.2 | 20 | 10 | o | ◎ |
| 22 | 50 | 10 | 50 | 70 | 0.3 | 30 | 20 | ◎ | o |
| 23 | 50 | 10 | 50 | 70 | 0.5 | 40 | 20 | ◎ | ◎ |
| 24 | 50 | 15 | 55 | 70 | 0.2 | 20 | 20 | ◎ | o |
| 25 | 70 | 30 | 65 | 100 | 0.2 | 20 | 20 | ◎ | o |
| 26 | 80 | 40 | 70 | 100 | 0.5 | 40 | 50 | ◎ | Δ |
| 27 | 100 | 50 | 80 | 120 | 0.2 | 20 | 20 | ◎ | ◎ |

[Embodiment 3]

The present embodiment is a modification of the oxygen concentration detector shown in FIG. 4 in which the poisonous durability is drastically improved by making the trap layer to a gradation structure in which the porosity continuously increases from the electrode protecting layer 2 to the surface in such manner as to trap poisonous substances stepwise, and the content thereof will be hereinafter described in full detail.

Figure 9:
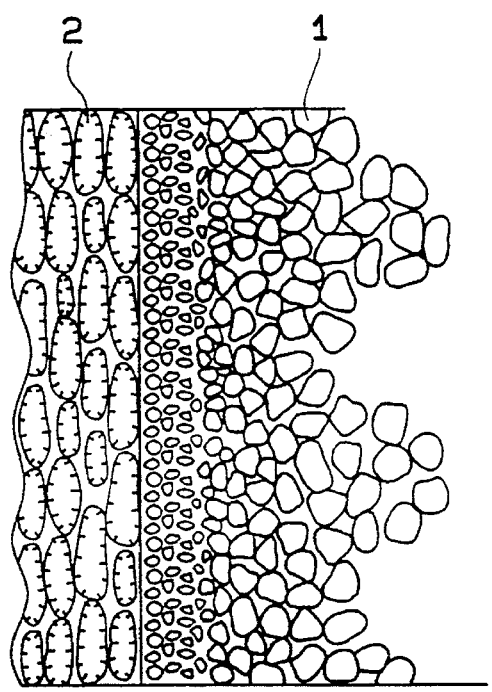
FIG. 9 is an enlarged sectional view of an oxygen sensing element, part of an oxygen concentration detector according to the embodiment 3 of the present invention.

As shown in FIG. 9, the oxygen sensing element 91 comprises a pair of outside electrode 31 and inside electrode 32, a porous electrode-protecting layer 2 for protecting the outside electrode 31 and controlling the diffusion of gas. The first trap layer 1 comprises a porous member for trapping a poisonous component as shown in FIG. 9. The electrode protecting layer 2 is a porous protective layer formed by flame fusion coating of $MgO.Al_2O_3$ spinel or the like. The first trap layer 1 is a porous member formed of numerous particles as shown in FIG. 9. These particles are thermally stable and continuously combined to form the first trap layer 1.

The above trap layer 1 is so structured that the outermost surface layer comprises coarse particles and exhibits a surface roughness of 20 μm or more in terms of 10 point average roughness ($R_z$), the content of fine particles gradually increases and the trap layer becomes dense toward the interior, and the innermost layer surpasses in porosity the electrode protecting layer 2.

Such the trap layer 1 is formed, that is, as follows: First, prepare six different grain size group of particles, ranging from 4 μm to 30 μm in average grain size at equal intervals. Add 3 to 20 wt % of inorganic binder as well as dispersant and water to 100 wt % of particles for each different size group to prepare a slurry. Form the trap layer 1 by depositing each slurry on the surface from the smallest to the largest in average grain size by dipping or by spraying and baking the deposits at 500° to 900° C. Alternatively, add 3 to 20 wt % of inorganic binder as well as dispersant and water to 100 wt % of the particle mixture of different grain size particles obtained according to the above method to form a slurry. The trap layer 1 is formed by depositing this slurry on the surface of a sensor. Here, on stirring the slurry with a stirrer or the like, particles of larger grain size gather at the peripheral portion of the vessel, particles of smaller grain size gather at the center, and a grain size distribution of sequentially increasing from the center to the periphery is generated. The trap layer 1 is deposited by inserting a sensing element into the center slurry portion of small grain size, moving it toward the periphery slurry portion of large grain size, and lifting the sensor element at the outermost slurry portion of the largest grin size. The trap layer 1 is formed by further baking the trap layer 1 deposited in this way at 500° to 900° C.

The porosity distribution and surface roughness $R_z$ of the trap layer 1 can be controlled by determining the grain size or mixing manner of particles to be used in preparing a slurry, or the speed of stirring or the position of dipping. The thickness T of the trap layer 1 must be not smaller than 10 μm at the thinnest portion to take advantage of the function of the trap layer and is preferably 30 μm or greater since the surface roughness must be 20 μm or greater for preventing the clogging of exhaust gas even if a glassy poisonous deposit sticks to the surface, and preferably 500 μm or smaller to achieve a good initial characteristic and an adhesive force between the trap layer 1 and the electrode protecting layer 2.

The trap layer 1 preferably comprise heat-resisting particles of one or more of $\alpha-Al_2O_3$, $\gamma-Al_2O_3$, murite, $MgO.Al_2O_3$ spinel, and $TiO_2$. The shape of particles may be selected out of globular, lump, plate, fiber, foam, pillar, needle and the like shapes.

Figure 10:
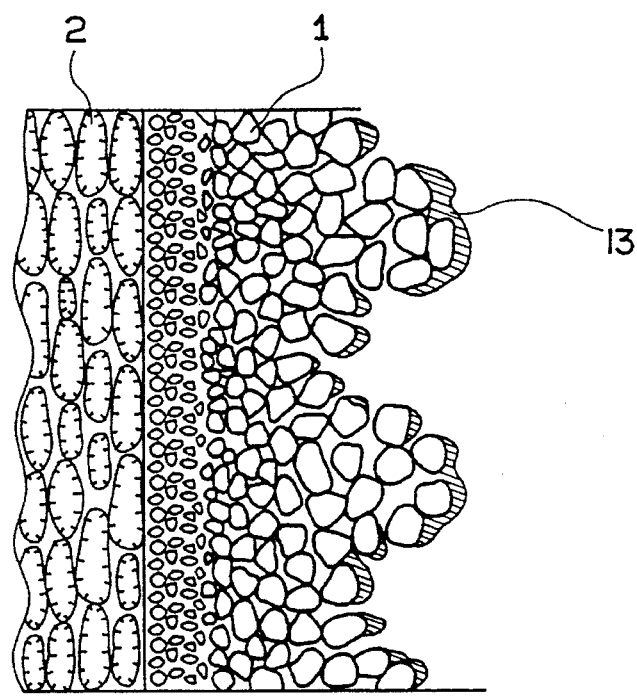
FIG. 10 is a schematic drawing illustrating the sticking aspect of a deposit on the surface of a trap layer of an oxygen sensing element, part of an oxygen concentration detector according to the embodiment 3 of the present invention.

According to the structure, even if a glassy poisonous substance is deposited under practical conditions, the roughness of the outermost surface causes a deposit to be interrupted at the boundary between a concave portion and convex portion (FIG. 10), thereby eliminating the possibility of the whole surface to be covered in the trap layer 1 and ensuring the opening portion to be maintained and consequently no deterioration of a sensor output. In addition, because fine poisonous substances are trapped in the trap layer 1, a poisonous substance 13 is prevented from reaching the electrode protecting layer 2 to cause a clogging. Furthermore, because fine poisonous substances are stepwise trapped in the trap layer 1 gradually varying in ventilating pores, the whole trap layer 1 can be thinned in comparison with the structure of the embodiment 1 and that of the embodiment 2. From these, a stable sensor characteristic can be maintained for a still longer period than that of the embodiments 1 and 2.

Figure 11:
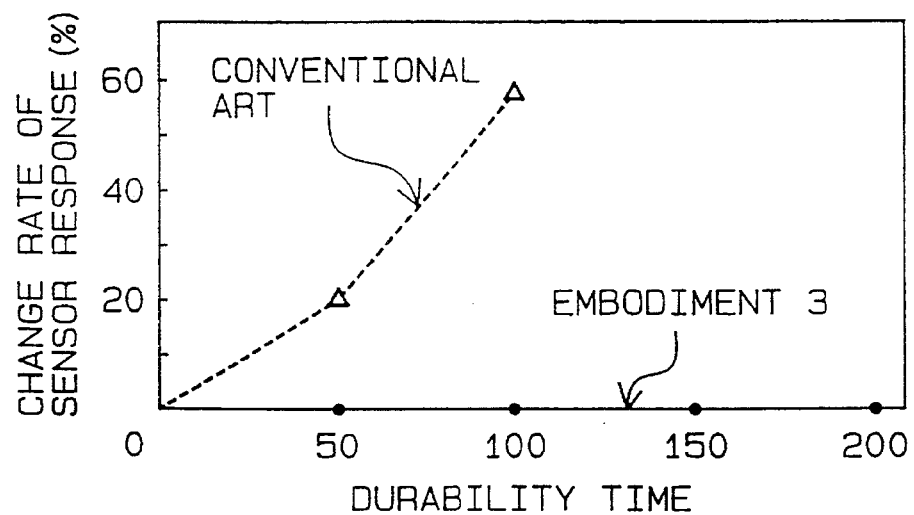
FIG. 11 is a graph representing the dependence of sensor response on endurance time in an oxygen concentration detector according to the embodiment 3 of the present invention.

Oxygen sensing elements 91 of the present invention were fabricated incorporating the trap layer 1 formed in accordance with the fabrication methods shown above. FIG. 11 shows the results of measurements on the dependency of the response on the endurance time for inventive oxygen concentration detector 91.

Measurements on endurance test conditions and response was performed using a method similar to that of the embodiment 1. The thickness T and surface roughness $R_z$ of the trap layer 1 are 100 μm and 50 μm, respectively. The trap layer 1 was formed by using six slurries different in average grain size, depositing each slurry on the surface from the smallest to the largest in average grain size by dipping or by spraying, and baking the deposits at 500° to 900° C. Table 3 shows the measured results of average pore diameter and porosity for each layer.

TABLE 3

| Layer | Average pore diameter d | Porosity |
|---|---|---|
| 1st layer | 0.3 | 30 |
| 2nd layer | 0.8 | 40 |
| 3rd layer | 2 | 45 |
| 4th layer | 5 | 50 |
| 5th layer | 10 | 60 |
| 6th layer | 15 | 70 |

[Embodiment 4]

The present embodiment is a modification of the oxygen concentration detector 90 shown in Embodiments 1 to 3 in which is found a method for making poison resistance compatible with durability while securing a bonding force between particles forming a trap layer, and the content thereof will be hereinafter described in full detail.

Figure 12:
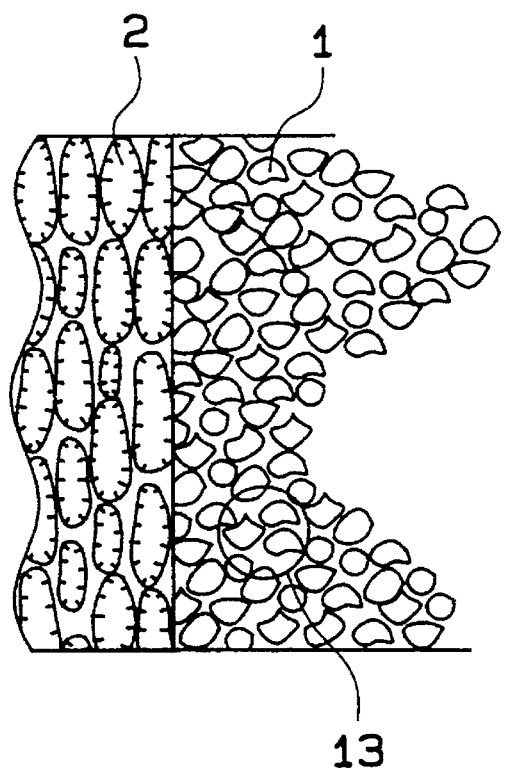
FIG. 12 is an enlarged sectional view of an oxygen sensing element, part of an oxygen concentration detector according to the embodiment 4 of the present invention.

As shown in FIG. 12, the oxygen sensing element 91 comprises a pair of outside electrode 31 and inside electrode 32, a porous electrode-protecting layer 2 for protecting the outside electrode 31, and the trap layer 1 covering the electrode protecting layer 2. The trap layer 1 consists of a porous member for trapping a poisonous component as shown in FIG. 12. The electrode protecting layer 2 is a porous protective layer formed by flame fusion coating of $MgO.Al_2O_3$ spinel or the like. As shown in FIG. 12, the trap layer 1 is a porous member formed of numerous particles. These particles are thermally stable and continuously combined to form the trap layer 1. The trap layer 1 has the outermost surface comprising coarse particles and exhibits a surface roughness of 20 μm in 10 point average roughness ($R_z$).

Such the trap layer 1 is formed, for example, as follows: First, add inorganic binder, dispersant, and water to $\gamma-Al_2O_3$ particles, 20 μm in average grain size, to prepare a slurry. Deposit this slurry on the surface of the oxygen sensing element by dipping, further bake the deposit at 500° to 900° C. to form the trap layer 1. The particles constituting the trap layer 1 acquire a binding force between the particles by baking at the temperature mentioned above, where the particles and the inorganic binder is absolutely required to be of the same kind. To be concretely, baking of the trap layer 1 must be performed in the temperature range mentioned above, but at such temperatures an adhesive force between particles becomes weak. Thus, on using a binder which turns to the same nature as with the particles after baking, the inorganic binder turns to the same nature as with the particles in the baking process and a bridged structure is formed between particles, thereby generating a binding force between particles.

When using an organic binder, however, the binder scatters due to burning or the like on the baking process and cannot contribute to the binding between particles, thereby leading to peeling off of the trap layer 1 because of weakened binding force. Peeling off occurs due to vibration or thermal stress even there is no such peeling off during he stage of forming the trap layer 1.

Figure 13:
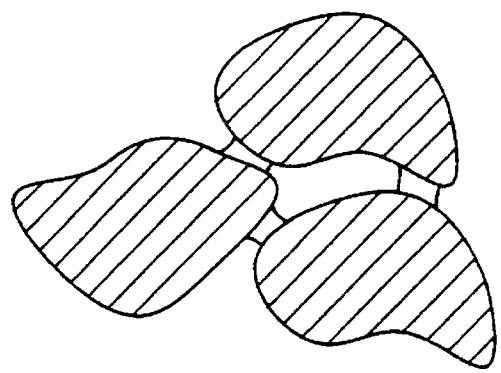
FIG. 13 is a state representation of joining of heating-resisting particles in a trap layer of an oxygen concentration detector according to the embodiment 4 of the present invention.

In the present embodiment of using $\gamma$-$Al_2O_3$, using alumina sol which turns to the same kind as with the particle after baking enables the particles to become homogeneous with the inorganic binder on a 500° to 900° C. baking process after deposition by dipping, and consequently a firm binding force is achieved (FIG. 13).

The amount of an inorganic binder to be used is preferably 3 to 20 wt % relative to the weight of the particles. That is, when the amount of binder is too small, only a small amount of binder is present between particle and accordingly a binding force for combining particles with each other cannot be obtained. On the contrary, when the amount of binder is too large, a binder force between particles is indeed obtained but an excess of binder not concerned in the binding of particles is likely to be accumulated in and stop up pores of the trap layer 1 or to entirely cover the particles, thereby damaging the capability of trapping a poisonous substance. By controlling the kind or amount of inorganic binder, the trap layer having average pore diameter of 0.5 μm or larger, porosity of 40 to 90%, and thickness of 30 to 500 μm, excellent in poison resistance and durability can be formed. The trap layer 1 preferably comprises heat-resisting particles of one or more of $\alpha$-$Al_2O_3$, $\gamma$-$Al_2O_3$ murite, $MgO.Al_2O_3$ spinel, and $TiO_2$.

The shape of particles may be selected out of globular, lump, plate, fiber, foam, pillar, needle and the like shapes. By controlling the amount of inorganic binder to turn to the same kind as with the particles after baking within the range of 3 to 20% relative to the weight of the particles, the trap layer 1 provided with poison resistance and durability together can be formed in the above materials and particle shapes, and a stable characteristic for sensing the oxygen concentration can be maintained for a long period.

In accordance with the fabrication method mentioned above, the trap layer 1 was formed and an oxygen sensing element 91 of the present invention was fabricated. Here, $\gamma$-$Al_2O_3$ was used as constituent particles of the trap 1, alumina sol was used as inorganic binder which turns to the same kind as with the particles after baking, and the amount of inorganic binder was varied between 1 to 30 wt %.

These experimental results have revealed that a binding force between particles is secured, no deterioration of the initial characteristic occurs, and a good poisonous durability is obtained when adding 3 to 20 wt % of inorganic binder that turns to the same kind as with the constituent particles after baking relative to the weight of the particles. Table 4 shows several examples of these experimental results.

Measurements on endurance test conditions and response were carried out using a method similar to that of the embodiment 1. The criteria for initial response and poisonous durability are similar to those of the embodiment 1. Values of adhesive force were estimated by taping, those of the trap layer peeled off and not peeled off were decided as o and as x, respectively.

Incidentally, needless to say the trap layers in the embodiments 1 to 4 are effective not only for a cup-type oxygen sensing element used in the present embodiment but also for laminated-type oxygen sensing element. Not only for an oxygen concentration electromotive sensor but also for oxide semiconductor detector, further leak sensor of marginal current oxygen concentration detector, air-fuel ratio sensor and the like, using the present constitution presents a similar effect.

TABLE 4

| No | Amount of binder (Wt %) | Mean pore diameter d (μm) | Porosity (%) | Thickness of the trap layer T (μm) | Surface roughness Rz (μm) | Adhesive force | Initial response | Poisonous durability |
|---|---|---|---|---|---|---|---|---|
| 28 | 1 | 5.5 | 60 | 50 | 20 | x | ⊙ | x |
| 29 | 2 | 5.5 | 60 | 50 | 20 | x | ⊙ | x |
| 30 | 3 | 5.5 | 60 | 100 | 20 | o | ⊙ | o |
| 31 | 5 | 5 | 55 | 200 | 20 | o | ⊙ | ⊙ |
| 32 | 5 | 5 | 55 | 100 | 20 | o | ⊙ | ⊙ |
| 33 | 7 | 5 | 50 | 100 | 20 | o | ⊙ | ⊙ |
| 34 | 10 | 5 | 50 | 100 | 20 | o | ⊙ | ⊙ |
| 35 | 15 | 5 | 50 | 100 | 20 | o | ⊙ | ⊙ |
| 36 | 20 | 4 | 45 | 100 | 20 | o | o | o |
| 37 | 20 | 4 | 45 | 100 | 20 | o | o | o |
| 38 | 25 | 3 | 35 | 100 | 15 | o | Δ | x |

[Advantages of the Invention]

In this way, it becomes possible to provide an oxygen concentration detector, with an dense air-tight glassy deposit coat prevented from forming on the surface of an oxygen sensor element, free from clogging and excellent in durability, that is, enabling a stable sensor output to be maintained for a long period.

[Embodiment 5]

Another oxygen sensor element fabrication method related to the embodiments of the present invention will be described referring to FIGS. 14 to 17.

An oxygen sensor element to be fabricated according to the present embodiment is of oxygen concentration electromotive type and used for detecting the oxygen concentration in exhaust gas of an automobile internal combustion engine.

Figure 14:
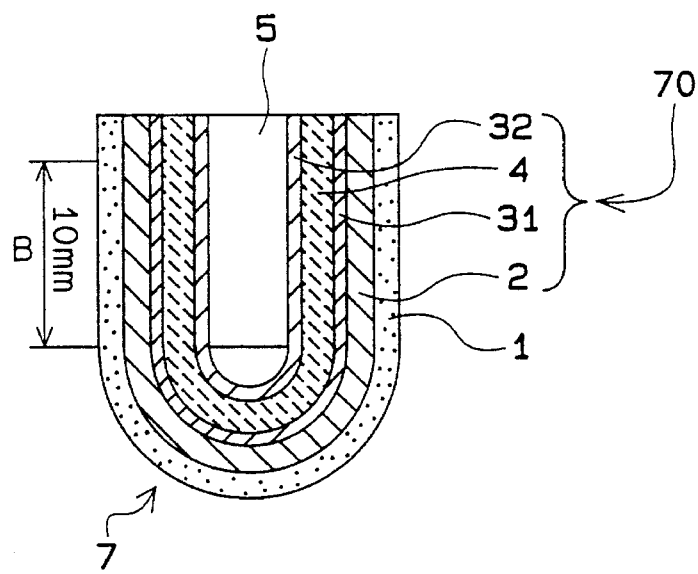
FIG. 14 is a sectional view of an oxygen sensor element according to the embodiment 5.

As shown in FIG. 14, the oxygen sensor element 7 comprises a one-end closed cup-shaped solid electrolyte 4, a pair of outside electrode 31 and inside electrode 32 provided on the respective sides of the solid electrolyte 4, a porous protective layer 2 covering the surface of the outside electrode 31, and a poisonous substance trap layer 1 covering the protective layer 2.

Figure 15:
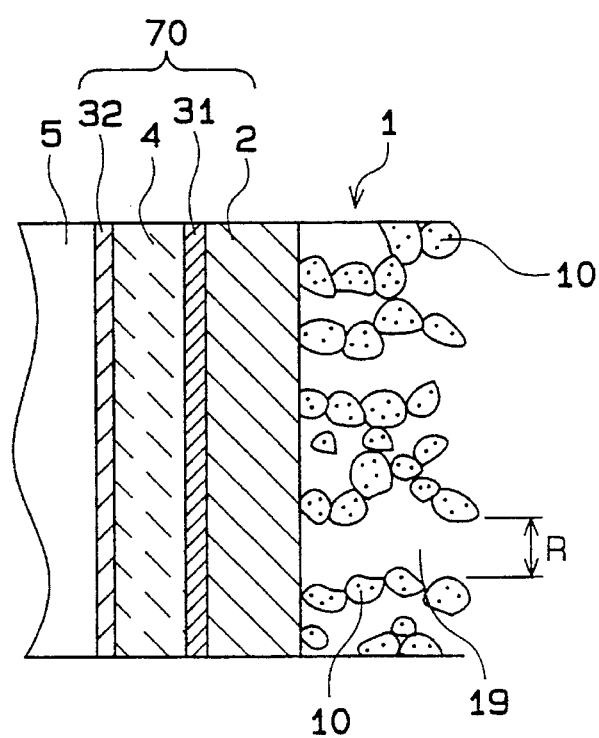
FIG. 15 is an enlarged principal sectional view of an oxygen sensor element according to the embodiment 5.

As shown in FIG. 15, the poisonous substance trap layer 1 is a dense porous member for trapping a poisonous component and comprises clusters of heat-resisting metal oxide particles 10. The protective layer 2 is formed by flame fusion coating of $MgO.Al_2O_3$ spinel or the like for protecting an electrode and controlling the diffusion. Solid electrolyte 4 comprises $ZrO_2$. The outside electrode 31 and inside electrode 32 are made of Pt.

Figure 16:
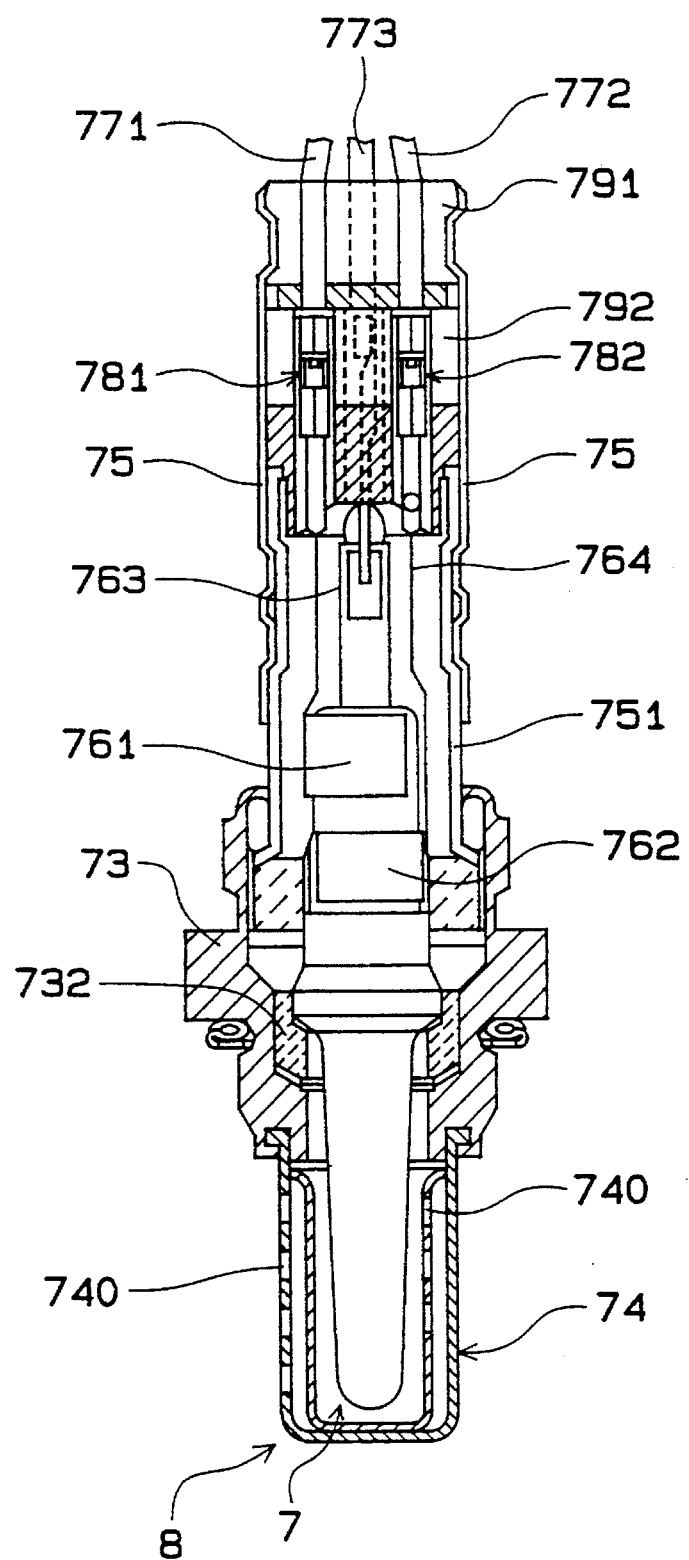
FIG. 16 is a sectional view of an oxygen sensor according to the embodiment 5.

As shown in FIG. 16, the oxygen sensor element 7 is loaded on the tip of an oxygen sensor 8. That is, the oxygen sensor element 7 is fixed via an insulating member 732 to a cylindrical metal housing 73.

To the lower opening of the housing 73 is attached a bottomed bicylindrical protective cover 74 provided with numerous ventilating holes 740. The oxygen sensor element 7 is disposed in the protective cover 74.

To the upper opening of the housing 73 is fixed a main body cover 751. Above the main body cover 751, a connector cover 75 for covering insulating members 791 and 792 is attached. In the insulating member 791, output pickup lead wires 771, 772 and a heater lead wire 773 are disposed. Output pickup lead wires 771 and 772 is electrically connected via connectors 781 and 782, electrode leads 763 and 764, and plate terminals 761 and 762 to the outside electrode 31 and inside electrode 32. The heater lead wire 773 is electrically connected to a heater 5 inside the oxygen sensor element 7.

Figure 17:
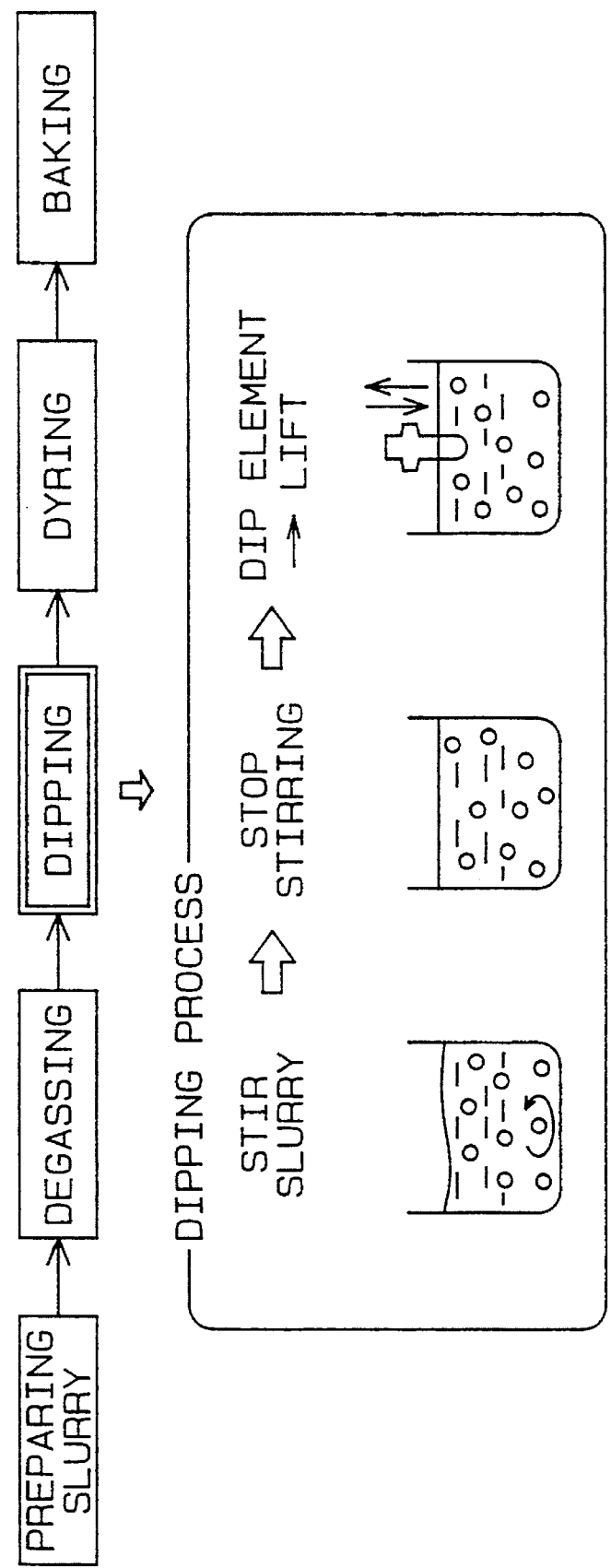
FIG. 17 is an explanatory drawing illustrating a method for forming a trap layer according to the embodiment 5.

Next, a fabrication method for the oxygen sensor element 7 attached to the oxygen sensor 8 will be described referring to FIGS. 14 and 17.

First, form an outside electrode 31 and inside electrode 32 outside and inside the one-end closed cylindrical solid electrolyte 4, one-end closed. Then, coat the surface of the solid electrolyte 4 with a protective layer 2 to prepare an oxygen sensor element 70.

Next, dip the exhaust-gas-side surface of the oxygen sensor element 70 in a slurry having heat-resisting metal oxide particles dispersed. Hereby, deposit the heat-resisting metal oxide particles onto the exhaust-gas-side surface of the oxygen sensor element 70. Thereafter, by drying, heating, and baking, form a porous poisonous substance trap layer 1.

The above dipping is performed after a previous degassing and strong stirring of the slurry and the completion of stirring.

Now, a method for forming the poisonous substance trap layer will be described.

First, prepare a slurry, 400 mPa.s in viscosity (25° C., B-type viscosimeter), by adding alumina sol, aluminum nitrate, and water to heat-resisting metal oxide particles, 20 μm in average grain size. These heat-resisting metal oxide particles are made of $\alpha$-$Al_2O_3$, $\gamma$-$Al_2O_3$, murite, $MgO.Al_2O_3$ spinel, $TiO_2$ or the like. Also, the heat-resisting metal oxide particles can be formed of secondary particles formed of clusters of primary particles, 2 μm or smaller in grain size.

Next, degas this slurry for 45 minutes under a reduced pressure of 4 kPa. Then, dip the oxygen sensing element 70 in this slurry to form a poisonous substance trap layer 1 on the protective layer 2 under the following conditions: Stir the degassed slurry strongly for 30 seconds. Start dipping the oxygen sensing element 70 after 15 seconds have passed from the completion of stirring. The dipping process was performed with the lowering speed and lifting speed of the oxygen sensing element 70 kept constant in the slurry. Complete the lifting after 20 seconds have passed from the start of dipping and finish the dipping. In this way, the slurry is deposited on surface of the protective layer 2 of the oxygen sensing element 70.

The conditions for the stirring are as follows: Stir the slurry at 600 rpm, say, with a magnetic stirrer. The lowering speed and lifting speed of the oxygen sensing element 70 are 20 mm/s and 1.5 mm/s, respectively.

Then, dry the poisonous substance trap layer 1 naturally for an hour and further at 120° C. for 30 min. Thereafter, baking heat-resisting metal oxide particles 10 on the surface of the protective layer 2 by 700° C. heat treatment to form a poisonous trap layer 1 finally. The thickness of the poisonous trap layer 1 is 60 μm.

Thus, an oxygen sensor element 7 shown in FIG. 14 is obtained.

A poisonous substance trap layer 1 uniform in film thickness and free from gas bubble was obtained in accordance with the fabrication method. The degree of uniformity in thickness was less than ±20% in the area B, 10 mm distant from the closed end, except for the semispherical part of the oxygen sensor element 70. The thickness was determined by observing the section with SEM and evaluating the largest difference between the protrusion and recess within the limits of 200 μm length.

Repeating the dipping further 30 times continuously, a poisonous substance trap layer was formed on the oxygen sensor element n=30. At that time, the variance in the deposit weight of a slurry was within 3% of relative standard deviation, showing a good result.

As for air bubbles, as shown in FIG. 15, the number of through holes 19, not smaller than 50 μm in caliber R, was less than 5 in the surface area 4 $cm^2$ of the poisonous substance trap layer 1.

Thus, it is found that a poisonous substance trap layer 1 uniform in film thickness and free from air bubble can be formed by dipping and an oxygen sensor excellent in trapping a poisonous substance and stable in sensor characteristic can be fabricated.

[Embodiment 6]

Figure 18:
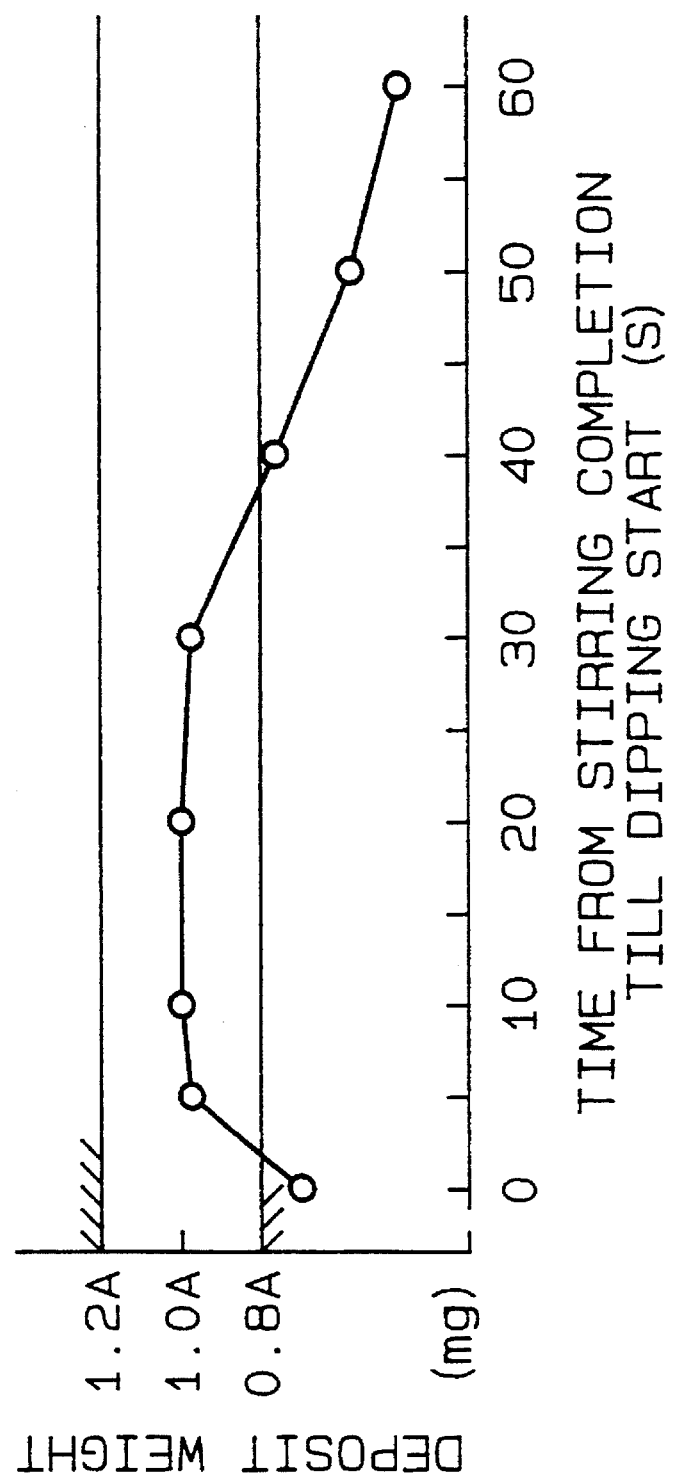
FIG. 18 is a correlation diagram illustrating the relationship between the time from the stop of stirring a slurry till the start of dipping and the deposit weight of slurry in an oxygen sensor element fabrication method according to the embodiment 6.

To measure a variance in the thickness of poisonous substance trap layers, the deposit weight of a slurry, and a variance in deposit weight, the present embodiment uses a variety of dipping conditions in the method for fabricating an oxygen sensor element according to the embodiment 5. Table 5 and FIG. 18 show the measured results.

For this measurement, a slurry, 400 mPa.s in viscosity, containing heat-resisting metal oxide particles ($\gamma$-$Al_2O_3$), 20 μm in average grain size, was used and degassed under the same conditions as with the embodiment 5. Then, stir this slurry in accordance with the following stirring method and dip an oxygen sensing element in the slurry. Other conditions than the stirring method and time taken since the completion of stirring till the start of dipping are similar to those of the embodiment 5.

Stirring was performed at 600 rpm for 30 s with a magnetic stirrer. After the completion of stirring, dipping was performed with the lowering speed and lifting speed of the oxygen sensing element made 20 mm/s and 1.5 mm/s in the slurry. Cases where the time from the completion of the stirring till the start of dipping is 0, 3, 5, 15, 30, and 40 seconds are represented by samples 2, 3, 4, 5, 6, and 7 related to the present invention (Table 5).

Incidentally, a case of performing the dipping while stirring was represented by the sample C1 for comparison. A case of stirring a slurry for 30 seconds, stopping the stirring, and starting the dipping after 15 seconds have passed from the completion of stirring is represented by the sample C8 for the comparison.

Then, a variation in the thickness of poisonous substance layers in the above samples C1, 2 to 7, and C8 was measured in accordance with a method similar to that of the embodiment 5.

dipping exceeds 30 seconds. This is attributable to the fact that most of the heat-resisting metal oxide particles sediment when time from the completion of stirring till the start of dipping is long.

If the deposit weight of a slurry is 0.8 to 1.2 Amg, a poisonous substance trap layer uniform in film thickness and excellent in trapping a poisonous substance can be formed. In this case, the sensor characteristic of an oxygen sensor element is also excellent.

TABLE 5

| Stirring | | | | Variance in film thickness x | Variance in deposit weight x | Sample | Control (while stirring) |
|---|---|---|---|---|---|---|---|
| Continuous stirring | | | | | | C1 | |
| Stirring 30 s ↓ Stop stirring ↓ Dipping | Repeated 30 times | Time from the completion of stirring till the start of dipping | 0 s | x | x | 2 | Present invention |
| | | | 3 s | Δ | Δ | 3 | |
| | | | 5 s | o | o | 4 | |
| | | | 15 s | o | o | 5 | |
| | | | 30 s | o | o | 6 | |
| | | | 40 s | o | Δ | 7 | |
| Without stirring* | | | | o | x | C8 | Control |

*30 s stirring ⟶ Stop stirring for 15 s ⟶ 30 continuous dipping

Next, a variation in the deposit weight of a slurry onto the surface of an oxygen sensing element was measured in the above samples C1, 2 to 7, and C8. The measuring method for the samples 2 to 7 is similar to that of the embodiment 1. For the sample C1, dipping was continuously performed 30 times while stirring the slurry. For the sample C8, the slurry was stirred for 30 seconds and stopped, the 1 st dipping was performed 15 seconds after the completion of stirring. The 2 nd dipping to the 30 th dipping were continuously performed without stirring the slurry.

Table 5 shows the results of the measurements.

In Table 5, the decision on a variance in film thickness was made as Δ and x for ±20% (inclusive) to ±30% g(exclusive) and for ±30% or greater in the area (B of FIG. 14) 10 mm distant from the closed end except for the semispherical part of the oxygen sensing element.

The decision on variance in the deposit weight of slurries was made as o, Δ, and x when the relative standard deviation (σ/x̄×100) obtained was below 3%, 3% to 4% (exclusive), and 4% and greater after continuous 30 dipping treatments.

Then, the relationship between the time (s) from the completion of stirring till the start of dipping and the deposit weight of a slurry was measured and the results are shown in FIG. 18. The number n of measurements is 30. The deposit weight of a slurry is indicated with the target value made as Amg.

From Table 5, it is found that the variation in the thickness of a poisonous substance trap layer and the variance in the deposit weight of a slurry are both good when the time from the completion of stirring till the start of dipping is 3 seconds or longer (samples 3 to 7). Especially when the time from the completion of stirring till the start of dipping was 5 to 30 seconds (samples 4, 5, and 6), the best poisonous substance trap layer could be formed.

From FIG. 18 it is found that the deposit weight decreases when the time from the completion of stirring till the start of

[Embodiment 7]

To measure the generation of air bubbles, the present embodiment uses a variety of degassing conditions in the oxygen sensor element fabrication method according to the embodiment 5.

For this measurement, a slurry, 400 mPa.s in viscosity, containing heat-resisting metal oxide particles ($\gamma Al_2O_3$), 20 μm in average grain size, was used and degassed under the following conditions:

Then, as with the embodiment 5, stir this slurry, dip an oxygen sensing element in the slurry after the completion of stirring, and form a poisonous substance trap layer by drying and baking. Other fabrication conditions than the degassing one are similar to those of the embodiment 5.

As shown in Table 6, degassing of a slurry was performed for varied pressure and duration to form the samples 11 to 15 according to the present invention. For comparison, fabrication was performed without degassing and the sample C16 was obtained.

With respect to the oxygen sensor element, the generating frequency of air bubbles was measured in an poisonous substance trap layer, where the air bubbles mean holes of caliber not smaller than 50 μm penetrating through the poisonous substance trap layer.

Table 6 shows the measured results.

The criterion for the generation of air bubbles in Table 6 is defined as o, Δ, and x when the number of through holes of 50 μm or more in the poisonous substance trap layer is below 5, 5 to 10 (exclusive), and above 10 for surface area of 4 $cm^2$.

As a result of measurements, the samples 11 to 15 related to the present invention had a smaller number of through holes than that of the control C16. Especially in the samples 14 and 15, the number of through holes was below 5 and markedly small. From these it is found that a good poisonous substance trap layer, scarce in air bubble, is obtained when the degassing condition is of pressure 5 to 10 kPa and not shorter than 30 minutes. Here, air bubbles mean through holes into which air bubbles turned when an air-bubble-contained slurry was deposited on the oxygen sensor element by dipping, or broken holes generated after the air bubbles split open on drying.

Incidentally, the poisonous substance trap layer may be formed in two, three, or more multiple layers, and at least one layer of those can be formed in accordance with the method of the present embodiment.

According to the methods for fabricating a poisonous substance trap layer shown in these embodiments 5 to 7, not only cup type but also laminated type trap layer can be formed on the surface of an oxygen sensing element. In a not only oxygen concentration electromotive sensor but also oxide semiconductor oxygen sensor, further leak sensor of marginal current oxygen sensor, air-fuel ratio sensor and the like, an excellent poisonous substance trap layer in the present invention can be formed.

TABLE 6

| Sample | Degassing conditions | | Air bubble generations |
|---|---|---|---|
| | Pressure | Time | |
| Present invention | | | |
| 11 | 50 kPa | 60 min | x |
| 12 | 20 kPa | 30 min | x |
| 13 | 20 kPa | 60 min | Δ |
| 14 | 10 kPa | 30 min | o |
| 15 | 5 kPa | 30 min | o |
| Control C16 | Without degassing | | Generation of numerous air bubbles |

In the above embodiments, the present invention is summarized as follows:

The degassing of the slurry is preferably performed under a reduced pressure of 3 to 10 kPa and for 30 min to 5 hr.

Implementing a reduced pressure environment less than 3 kPa requires too much cost but no technical benefit is expectable to counterbalance the cost. On the other hand, for a pressure above 10 kPa, degassing becomes insufficient, air bubbles remain in the deposited slurry and split off on drying, a large air bubble is generated in the poisonous substance trap layer after baking and numerous through holes penetrating the trap layer are likely to be formed. In this case, it seems probable that the effect of trapping a poisonous substance lowers in the trap layer or variations appear in the sensor characteristic.

In degassing for shorter than 30 minutes, the degassing sing becomes insufficient and so it seems similarly probable that the effect of trapping a poisonous substance lowers or variations appear in the sensor characteristic. On the other hand, in degassing for longer than 5 hours, too much cost is needed but no technical benefit is expectable to counterbalance the cost.

After the above degassing, stir the slurry strongly. A strong stirring means, say, such a degree of stirring that heat-resisting metal oxide particles in the slurry are almost flowing. As a method for stirring a slurry, that is, there is a method for stirring a slurry at an appropriate rotational speed according to the state thereof with a magnetic stirrer. The rotational speed of a magnetic stirrer is set, say, at 100 to 1000 rpm.

The timing of the dipping is preferably performed as follows: Stir a slurry for 30 s to 10 minutes strongly, start the dipping 5 to 30 seconds after the completion of stirring, continue dipping with the lowering speed and lifting speed of an oxygen sensing element kept respectively constant in the slurry. Complete the lifting of the oxygen sensor element for 5 to 30 seconds after the start of dipping and end the dipping.

In this way, the best poisonous substance trap layer, uniform in film thickness and scarce in bubbles can be formed.

The lowering speed and lifting speed of an oxygen sensing element are preferably 1 to 30 mm/s and 0.5 to 3 mm/s, respectively. In this way, slurry can be deposited at the most uniform thickness on the surface of a protective layer.

In dipping numerous oxygen sensing element, the stirring of the slurry, the stop of stirring, and the dipping of an oxygen sensing element are repeated.

After the completion of the dipping, the deposited slurry is dried. This drying proceeds as natural drying, heat drying, and the like. After drying, heat-resisting metal oxide particles are baked on the surface of an oxygen sensing element by a heat treatment to form a poisonous substance trap layer.

The drying and baking mentioned above is preferably performed as follows: For example, naturally dry the poisonous substance trap layer for 30 minutes to 5 hours after the completion of dipping, then dry it at 100° to 150° C. for 10 min to 2 hours, and further treat it at 450° to 900° C. on heating. In this way, the strength of a poisonous substance trap layer is improved and the occurrence of a crack can be prevented in the poisonous substance trap layer.

This is because an abrupt heat drying or heat treatment without drying will cause the moisture in the slurry layer to evaporate abruptly therefrom, possibly inducing a crack to be generated in a poisonous substance trap layer.

In this present invention, the viscosity of the slurry is preferably 10 to 2000 mPa.s (25° C., B-type viscosimeter). For a viscosity below 10 mPa.s, heat-resisting metal oxide particles easily sediment and are most likely not to stick to an oxygen sensor element during dipping. On the other hand, for a viscosity above 2000 mPa.s, the viscosity is too high and the slurry is nearly pasty, thereby making an even dipping unable. The slurry comprises preferably heat-resisting metal oxide particles, alumina sol, aluminum nitrate, and water. In this case, slurry can be evenly deposited on the surface of a protective layer.

The heat-resisting metal oxide particles comprises one or more selected from a group of, say, $\gamma$-$Al_2O_3$, $\alpha$-$Al_2O_3$, murite, $MgO.Al_2O_3$ spinel, and $TiO_2$.

The heat-resisting metal oxide particles may be secondary particles formed out of a collection of primary particles, smaller than 2 μm in average grain size.

Variations in the thickness of the poisonous substance trap layer are preferably smaller than ±30%. For a thickness above ±30%, the object of the present invention becomes hardly achievable and the functional characteristic of an oxygen sensor element is likely to deteriorate.

When the poisonous substance trap layer is of a one-end closed cup-type, variations in thickness is preferably below ±30% in the area 10 mm distant from the closed end except for the semispherical portion thereof for the same reason as above, more preferably below ±20%.

Incidentally, because the functional characteristic is controlled nearly by the area 10 mm distant from the closed end except for the semispherical portion, the above variations are inessential concerning the semispherical portion in the closed end of the oxygen sensor element.

In the poisonous trap layer it is preferred that air bubbles as remains of air bubbles in the slurry are as scarce as possible. For a great number of air bubbles, a poisonous substance trap layer becomes likely to be less effective in trapping a poisonous substance. Preferably, through holes vertically formed in a straight line, especially by linkage of a plurality of air bubbles, is scarce.

Concretely, the number of through holes, 50 μm or more in caliber, vertically penetrating the poisonous trap layer is preferably made to be smaller than 5 for a surface area of 4 cm$^2$. For 5 or more of such through holes, it seems probable that the poisonous trap layer becomes less effective in trapping a poisonous substance or variations appear in the sensor characteristic of the oxygen sensor element.

The poisonous trap layer is a dense porous member having fine pores. Different from the remains of air bubbles contained in the slurry, these pores do not penetrate the poisonous trap layer in a straight line and concretely, are 0.5 to 30 μm.

The average grain size of the heat-resisting metal oxide particles is 2 to 50 μm. For average grain size below 2 μm, the ventilation of the poisonous substance trap layer decreases, whereas the flow rate of the gas to be detected cannot be controlled for average grain size above 50 μm.

The thickness of the poisonous substance trap layer is between 10–500 μm. When the thickness is less than 10 μm, the flow rate of the gas cannot be controlled. On the other hand, when the thickness is 500 μm or over, the ventilation of the poisonous substance trap layer decreases.

The oxygen sensor element comprises a solid electrolyte, a pair of electrodes provided on the respective surfaces of the solid electrolyte, and a protective layer covering the exhaust-gas side surface of the solid electrolyte. The solid electrode comprises, for example, $ZrO_2$-$Y_2O_3$. The protective layer comprises, for example, $MgO.Al_2O_3$ spinel for electrode protection and diffusion control. And, by forming a poisonous substance trap layer on this protective layer, an oxygen sensor element is prepared.

Oxygen sensor element according to the present invention includes, for example, a cup type made of one-end closed oxygen sensing element or a laminated type made by lamination on the surface of a sensing element. In addition, the oxygen sensor element is also applicable to a gas concentration electromotive sensor, marginal current sensor, or oxide semiconductor sensor.

What is claimed is:

1. An oxygen concentration detector for detecting oxygen concentration in a gas, comprising:

an oxygen sensing element including inside and outside electrodes provided on an inner side and outer side thereof respectively and an electrode protecting layer made of ceramics porous member provided further outside of said outside electrode;

output pickup means electrically connected to said inner electrode on said inner side of said oxygen sensing element;

a housing for accommodating said oxygen sensing element; and a trap layer of ceramics porous member having a surface roughness of 20 to 100 μm measured according to a 10 point mean roughness measurement and provided at an outerperiphery of the said electrode protecting layer.

2. The oxygen concentration detector as set forth in claim 1, wherein said electrode protecting layer is a flame fusion ceramics coating layer porous member, said trap layer is a ceramics porous member of heat-resisting particles comprising one or more of globular, block, fiber, foam, pillar, or needle $\alpha$-$Al_2O_3$, $\gamma$-$Al_2O_3$, murite, $MgO.Al_2O_3$ spinel.

3. The oxygen concentration detector as set forth in claim 1, wherein said trap layer is 50 to 500 μm in thickness.

4. The oxygen concentration detector as set forth in claim 1, wherein said trap layer is 0.5 to 50 μm in average pore diameter.

5. The oxygen concentration detector as set forth in claim 1, wherein said trap layer is 40 to 80% in porosity.

6. The oxygen concentration detector as set forth in claim 1, wherein said trap layer includes a first and second trap layers, said first layer is formed on said electrode protecting layer, said second trap layer is formed on said first trap layer, said first trap layer is more porous than said electrode protecting layer, and said first trap layer is denser than said second trap layer.

7. The oxygen concentration detector as set forth in claim 6, wherein said trap layer is made up to such a layered structure that the porosity increases from said electrode protecting layer side of said trap layer to the outer surface side thereof.

8. An oxygen concentration detector as in claim 1, wherein said trap layer is formed as an outer-most surface of the oxygen sensing element and exposed to the gas to be measured.

9. A fabrication method of an oxygen concentration detector having a cylindrical oxygen sensor element including an electrode protecting layer and a trap layer thereon, comprising the steps of:

preparing a slurry by dispersing heat-resisting particles comprising one or more of globular, block, fiber, foam, pillar, or needle $\alpha$-$Al_2O_3$, $\gamma$-$Al_2O_3$, murite or $MgO.Al_2O_3$ spinel, an inorganic binder, and a dispersant in water;

depositing said slurry onto said electrode protecting layer made of porous ceramics body so that an average grain size of said heat-resisting particles is 20 μm or more and the content of particles of 10 μm or less in grain size is not greater than 10 wt %; and baking said oxygen sensor element at 500° to 900° C. so that said trap layer has several layers of different average grain size of heat-resisting particles and has a surface roughness of 20 to 100 μm measured according to a 10 point mean roughness measurement.

10. The fabrication method of an oxygen concentration detector as set forth in claim 9, wherein said preparing step further includes preparing slurries of heat-resisting particles with different average diameter, said depositing step further includes depositing repeatedly said slurry with from small average diameter to large average diameter.

11. The fabrication method of an oxygen concentration detector as set forth in claim 9, wherein said slurry includes an inorganic binder which is the same kind as the heat-resisting particles and of which amount is 3 to 20 wt %.

12. The fabrication method of an oxygen concentration detector as set forth in claim 9, wherein said slurry is deposited onto said electrode protecting layer by dipping or spraying.

13. A fabrication method as in claim 9, wherein said trap layer is formed on an outer-most surface of the oxygen sensor element and exposed to the gas to be measured.

14. A fabrication method of an oxygen concentration detector comprising the steps of:

providing an oxygen sensor element by forming a pair of electrodes on the respective surfaces of a solid electrolyte and coating the to-be-detected gas side surface of said solid electrolyte with a porous protective layer;

depositing a slurry in which heat-resisting metal oxide particles, 2 to 50 μm in average grain size, are dispersed onto the surface of said protective layer by dipping; and forming a porous poisonous substance trapping layer, 10 to 500 μm thick, by drying and baking said heat-resisting metal oxide particles wherein said dipping is performed after the previous degassing and strong stirring of said slurry and the completion of stirring.

15. The fabrication method of an oxygen concentration detector as set forth in claim 14, wherein the degassing of said slurry is performed under reduced pressures of 3 to 10 kPa for 30 minutes to 5 hours.

16. The fabrication method of an oxygen concentration detector as set forth in claim 14, wherein said slurry is strongly stirred for 30 seconds to 10 minutes, said dipping starts 5 to 30 seconds after the completion of stirring, is performed with the constant lowering and lifting speed of said oxygen concentration, and ends with the completion of lifting said oxygen sensor element 5 to 30 seconds after the start of dipping.

17. The fabrication method of an oxygen concentration detector as set forth in claim 14, wherein said poisonous substance trap layer is naturally dried for 30 minutes to 5 hours after the completion of said dipping, then dried at 100° to 150° C. for 10 minutes to 2 hours, and baked at 450° to 900° C.

18. The fabrication method of an oxygen concentration detector as set forth in claim 14, wherein the viscosity of said slurry is 10 to 2000 mPa.s.

19. The fabrication method of an oxygen concentration detector as set forth in claim 14, wherein said slurry consists of heat-resisting metal oxide particles, alumina sol, aluminum nitrate and water.

20. The fabrication method of an oxygen concentration detector as set forth in claim 14, wherein said heat-resisting metal oxide particles consists of one or more selected from the group of $\alpha$-$Al_2O_3$, $\gamma$-$Al_2O_3$, murite, $MgO.Al_2O_3$ spinel, and $TiO_2$.

21. The fabrication method of an oxygen concentration detector as set forth in claim 14, wherein the variance in the thickness of said poisonous substances trap layer is smaller than $\pm 30\%$.

22. The fabrication method of an oxygen concentration detector as set forth in claim 14, wherein said poisonous substance trap layer has less than 5 through holes of not smaller than 50 μm caliber in 4 $cm^2$ of the surface area.

23. A fabrication method as in claim 14, wherein said trapping layer is formed on an outer-most surface of the oxygen sensing element and exposed to the gas to be measured.

* * * * *